US012614638B2

(12) United States Patent
Ionita et al.

(10) Patent No.: US 12,614,638 B2
(45) Date of Patent: Apr. 28, 2026

(54) METHOD FOR ASSESSING VASCULATURE, OBTAINING ANGIOGRAPHIC PARAMETRIC IMAGING (API) MAPS OF VASCULATURE AND DETERMINING STATE OF VASCULATURE USING MACHINE-LEARNING CLASSIFIER

(71) Applicant: The Research Foundation for The State University of New York, Amherst, NY (US)

(72) Inventors: Ciprian Ionita, Buffalo, NY (US); Mohammad Mahdi Shiraz Bhurwani, Buffalo, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 578 days.

(21) Appl. No.: 17/780,283

(22) PCT Filed: Nov. 27, 2020

(86) PCT No.: PCT/US2020/062524
§ 371 (c)(1),
(2) Date: May 26, 2022

(87) PCT Pub. No.: WO2021/108783
PCT Pub. Date: Jun. 3, 2021

(65) Prior Publication Data
US 2023/0000364 A1     Jan. 5, 2023

Related U.S. Application Data

(60) Provisional application No. 63/105,196, filed on Oct. 23, 2020, provisional application No. 62/941,701, filed on Nov. 27, 2019.

(51) Int. Cl.
*A61B 5/02* (2006.01)
*G06N 3/04* (2023.01)
(Continued)

(52) U.S. Cl.
CPC ......... *G16H 50/30* (2018.01); *A61B 5/02014* (2013.01); *G06N 3/04* (2013.01);
(Continued)

(58) Field of Classification Search
None
See application file for complete search history.

(56) References Cited

U.S. PATENT DOCUMENTS 7,218,702 B2 *   5/2007   Mistretta ................ A61B 6/025
                                              378/98.12
2005/0251010 A1   11/2005   Mistretta et al.
(Continued)

OTHER PUBLICATIONS

Podgorsak et al., "Use of a convolutional neural network for aneurysm identification in digital subtraction angiography," Progress in Biomedical Optics and Imaging, SPIE—International Society for Optical Engineering, Mar. 13, 2019, vol. 10950.
(Continued)

*Primary Examiner* — Haris Sabah
(74) *Attorney, Agent, or Firm* — Hodgson Russ LLP

(57) ABSTRACT

Methods and systems are provided for assessing a vasculature of an individual. In an embodiment of a method, one or more angiographic parametric imaging (API) maps of the vasculature are obtained, wherein each API map of the one or more API maps encodes a hemodynamic parameter. A state of the vasculature is determined using a machine-learning classifier applied to the one or more API maps.

34 Claims, 12 Drawing Sheets

(51) Int. Cl.

| | |
|---|---|
| *G06N 20/20* | (2019.01) |
| *G06T 7/00* | (2017.01) |
| *G06V 10/25* | (2022.01) |
| *G06V 10/44* | (2022.01) |
| *G06V 10/82* | (2022.01) |
| *G16H 50/30* | (2018.01) |
| *G06T 3/02* | (2024.01) |

(52) U.S. Cl.
CPC ........... *G06N 20/20* (2019.01); *G06T 7/0012* (2013.01); *G06V 10/25* (2022.01); *G06V 10/454* (2022.01); *G06V 10/82* (2022.01); *G06T 3/02* (2024.01); *G06T 2207/20081* (2013.01); *G06T 2207/20084* (2013.01); *G06T 2207/30101* (2013.01)

(56) References Cited

U.S. PATENT DOCUMENTS

| | | | |
|---|---|---|---|
| 2008/0192997 A1* | 8/2008 | Grass .................... | G06T 11/008 382/128 |
| 2009/0324052 A1* | 12/2009 | Nowinski ............. | G06T 7/0014 382/134 |
| 2014/0081131 A1* | 3/2014 | Kyriakou ............. | A61B 6/5264 600/425 |
| 2017/0213339 A1* | 7/2017 | Hibbard ................. | G06T 7/143 |
| 2018/0330484 A1 | 11/2018 | Bauer et al. | |
| 2019/0015061 A1 | 1/2019 | Liebeskind et al. | |
| 2019/0139219 A1 | 5/2019 | Isgum et al. | |
| 2019/0172205 A1 | 6/2019 | Mao et al. | |

OTHER PUBLICATIONS

Chandra et al., "Initial study of the radiomics of intracranial aneurysms using Angiographic Parametric Imaging (API) to evaluate contrast flow changes," Medical Imaging 2019: Physics of Medical Imaging, Mar. 1, 2019.

Rava et al., "Performance of angiographic parametric imaging in locating infarct core in large vessel occlusion acute ischemic stroke patients," Journal of Medical Imaging, Feb. 11, 2020, vol. 7, No. 1.

Brownlee et al., "Ensemble Learning Methods for Deep Learning Neural Networks," Machine Learning Mastery, Aug. 6, 2019.

* cited by examiner

100 ⟶

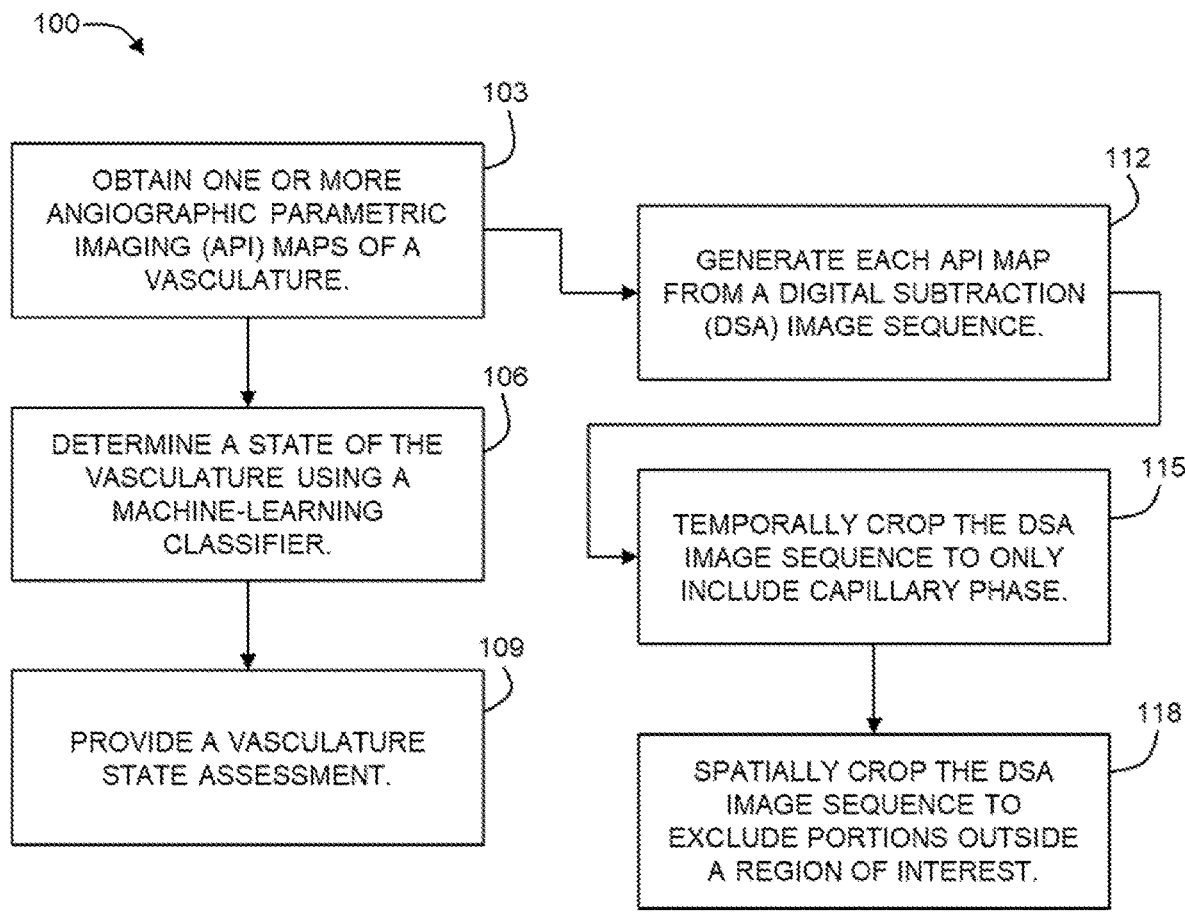

103

OBTAIN ONE OR MORE ANGIOGRAPHIC PARAMETRIC IMAGING (API) MAPS OF A VASCULATURE.

112

GENERATE EACH API MAP FROM A DIGITAL SUBTRACTION (DSA) IMAGE SEQUENCE.

106

DETERMINE A STATE OF THE VASCULATURE USING A MACHINE-LEARNING CLASSIFIER.

115

TEMPORALLY CROP THE DSA IMAGE SEQUENCE TO ONLY INCLUDE CAPILLARY PHASE.

109

PROVIDE A VASCULATURE STATE ASSESSMENT.

118

SPATIALLY CROP THE DSA IMAGE SEQUENCE TO EXCLUDE PORTIONS OUTSIDE A REGION OF INTEREST.

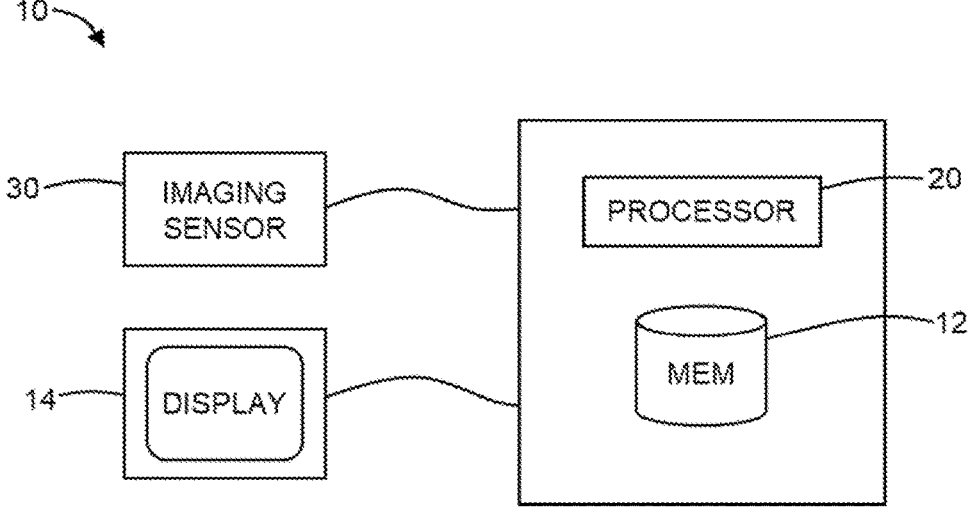

30 — IMAGING SENSOR

20 — PROCESSOR

12 — MEM

14 — DISPLAY

METHOD FOR ASSESSING VASCULATURE, OBTAINING ANGIOGRAPHIC PARAMETRIC IMAGING (API) MAPS OF VASCULATURE AND DETERMINING STATE OF VASCULATURE USING MACHINE-LEARNING CLASSIFIER

CROSS-REFERENCE TO RELATED APPLICATIONS

This application claims priority to U.S. Provisional Application Nos. 62/941,701, filed on Nov. 27, 2019, and 63/105,196, filed on Oct. 23, 2020, the disclosures of each are incorporated herein by reference.

FIELD OF THE DISCLOSURE

The present disclosure relates to angiographic parametric imaging (API), and more particularly to assessing vasculature using API.

BACKGROUND OF THE DISCLOSURE

The treatment of neurovascular disorders has seen many advances and a corresponding improvement in patient outcomes. For example, patients with emergent large vessel occlusion (LVO) acute ischemic strokes (AIS) account for 24%-46% of all AIS cases. While there are many confounding factors, timely recanalization of such blockages is essential for optimal patient outcome. Mechanical thrombectomies (MT) aim at endovascular retrieval of clots to restore blood flow to ischemic territories. MTs are reported to have successful reperfusion rates between 75%-80% compared to 30% early recanalization rate when using intravenous thrombolysis with recombinant tissue-type plasminogen activators. Thus, MTs have markedly reduced severe disability and mortality compared to intravenous thrombolysis, and have been established as the standard care for LVO AISs. However, intra-procedural assessment of reperfusion during MT for emergent LVO stroke is traditionally based on subjective evaluation of digital subtraction angiographs (DSA).

Hemodynamic factors such as flow patterns, wall shear stress, and velocity play important roles in the initiation, growth, and rupture of intracranial aneurysms (IAs). The aim of endovascular treatments such as coil embolization and flow diversion are to occlude the IAs and reduce the risk of rupture by modifying the hemodynamics in the aneurysmal dome. These therapies reduce the mechanical stress exerted on the aneurysm wall, while catalyzing the endovascular clotting cascade. For IAs treated with a Pipeline Embolization Device (PED), occlusion may occur after several months, and post-procedure follow-ups (for example, for six months post-treatment) are required to assess the IA's occlusion status. For IAs treated with a PED, 21.8% remain partially to completely un-occluded and there is currently no accurate imaging-based diagnosis tool, which may predict IAs at risk of poor outcome.

There is a need for improved techniques for assessing a vasculature of an individual immediately post-treatment (e.g., intra-procedurally) to more accurately predict outcome for the individual. In this way, a surgeon may better determine whether additional intervention is appropriate.

BRIEF SUMMARY OF THE DISCLOSURE

The present disclosure provides methods and systems for the use of data driven approaches, such as machine-learning classifiers (e.g., convolutional neural networks (CNN), etc.) with angiographic parametric imaging (API) maps to automatically assess the vasculatures of individuals during surgical procedures. In addition, normalization methods may be implemented to eliminate intra-operator and vessel architecture variability. Embodiments of the present disclosure may be suitable for use in the operating room to predict whether the intervention performed was successful or not based on the API data measured pre- and post-treatment. Embodiments of the present disclosure may be used to predict the treatment outcome in less than 3 milliseconds in a patient anywhere in the world. It can be created to run on a local machine or in a cloud.

The presently-disclosed techniques provide at least three advantages: First, an innovative (and more powerful) modeling approach. The present disclosure combines angiography and Machine Learning to quantitatively predict outcome at the time of treatment. Heretofore, neurovascular treatment has been conducted qualitatively, with no readily available quantitative tools exists to guide therapeutic decisions. Although computational flow dynamics tools exist, given computational time, they are mostly intended for treatment planning and do not use angiographic data generated in real-time. The present disclosure provide embodiments of an independent tool which may predict neuro-intervention outcomes at the time of treatment. Second, the present approach builds on continuing growth of imaging databases such as perfusion analysis angiography, MRI to use angiographically-derived correlates to perform predictions. Third, the present approach optionally uses unique methods to improve the robustness of the prediction software. For example, the present approach provides the ability to correct for imaging artifacts and reduce injection variability.

DESCRIPTION OF THE DRAWINGS

For a fuller understanding of the nature and objects of the disclosure, reference should be made to the following detailed description taken in conjunction with the accompanying drawings.

FIG. 1: A chart depicting a method according to an embodiment of the present disclosure.

FIG. 2: A diagram depicting a system according to another embodiment of the present disclosure.

DETAILED DESCRIPTION OF THE DISCLOSURE

Figure 3:
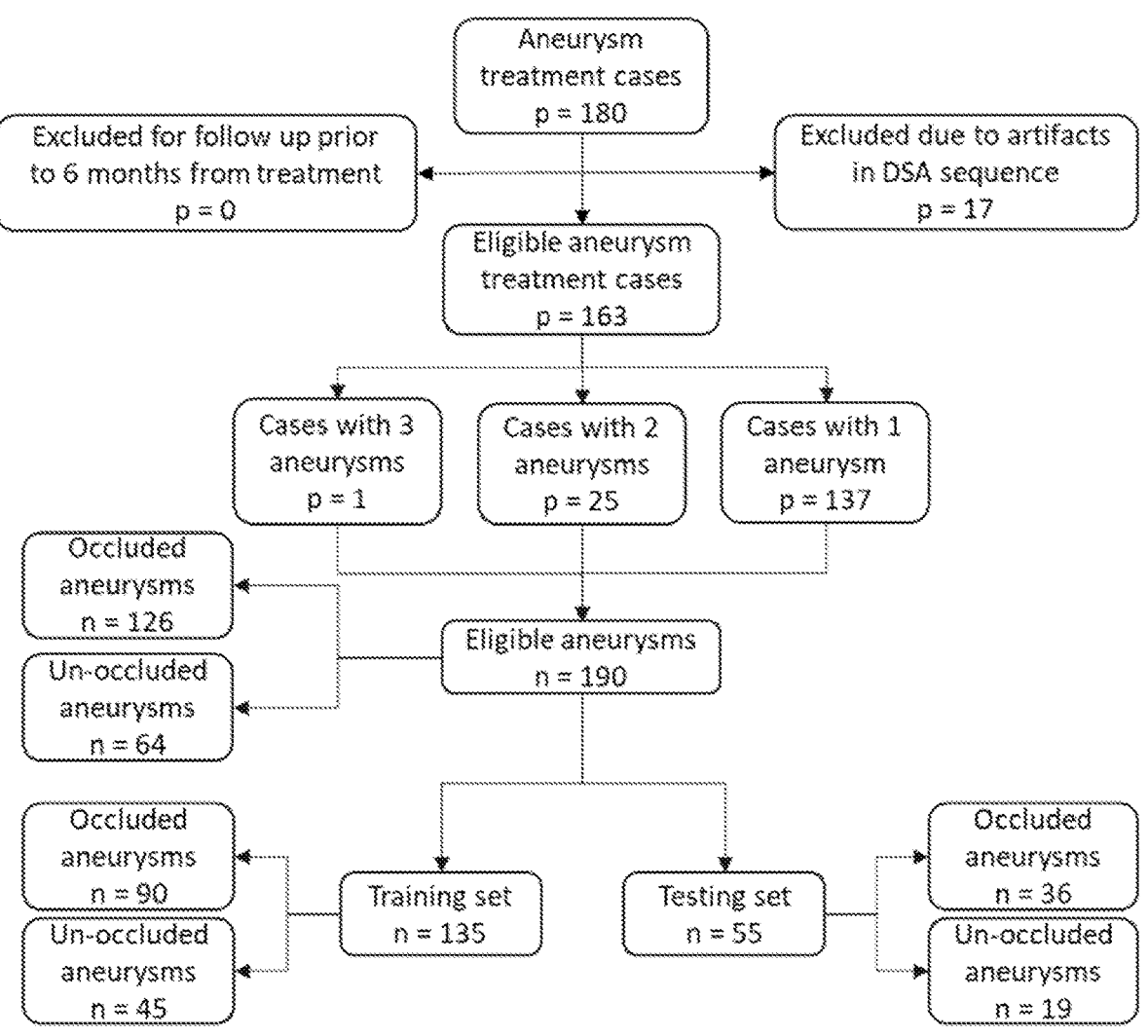
FIG. 3: Study inclusion schema. p refers to number of patients and n refers to number of IAs.

Since early in the development of neuro-digital subtraction angiography, many have attempted to utilize the temporal information of contrast propagation for diagnosis of disease or treatment outcome. Neurological applications are very well suited for such analysis due to aspects such as, for example, reduced patient motion, use of bi-plane systems that provide a second view plane, and selective injection wherein the contrast-introducing catheter is placed into a smaller artery of interest such that only a subset of arteries in a particular area of the brain is opacified, thus reducing the number of overlapping vessels.

Temporal information in a sequence of digital subtraction angiography (DSA) images may be used to create a parametrized description of blood flow over the entire vasculature and can be used to assess qualitatively aspects of the flow or evaluate treatment effects. Angiographic parametric imaging (API) maps are generated by analyzing the contrast behavior at each pixel in an angiogram over the entire time sequence. This method may use contrast Time Density Curves (TDCs) to calculate hemodynamic parameters such as Mean Transit Time (MTT), Time to Peak (TTP), and Bolus Arrival Time (BAT). Such parameters, which are common to other imaging modalities, such as CT perfusion, have been investigated in detail and their relation with certain medical conditions is well established.

In some embodiments, the presently-disclosed method utilizes angiographic contrast flow monitoring using high-speed angiography to build a time density curve at each pixel of a time sequence which contains a vessel. Next, each curve can be parametrized mathematically to calculate MTT, TTP, etc. Although there is some understanding of how individual biomarkers relate to neurovascular conditions, for instance that MTT, which is the average time spent by a contrast particle in a given region, is inversely related to the blood flow velocity of an aneurysm, and that an increased MTT is beneficial for clot aggregation formation, current knowledge of correlations between the imaging biomarkers and the vascular blood flow conditions is incomplete. Combining multiple pre- and post-treatment parameters creates complicated analyses with as-yet poorly understood relationships. The present disclosure makes use of machine learning to predict treatment outcomes based on angiographic parametric imaging.

With reference to FIG. 1, the present disclosure may be embodied as a method 100 for assessing a vasculature of an individual. For example, as further described below, the method may be used to assess a reperfusion status of the vasculature (i.e., a predicted reperfusion following a mechanical thrombectomy (MT)). In another example, the method may be used to assess an occlusion state of the vasculature (i.e., a predicted occlusion of an intracranial aneurysm (IA)). The method is useful for intra-procedural evaluation. For example, the method may be used during an endovascular procedure to predict the success of the intervention of the procedure.

The method includes obtaining 103 one or more angiographic parametric imaging (API) maps of the vasculature. For example, a pre-treatment API map may be obtained, and a post-treatment API map may be obtained. It should be noted that the term post-treatment is used herein to refer to a time following a treatment, including intra-procedurally (i.e., immediately post-treatment). Each API map of the one or more obtained 103 API maps encodes a hemodynamic parameter. The hemodynamic parameter can be any parameter found to be useful in predicting a state of the vasculature. For example, the hemodynamic parameter may be one or more of time to peak (TTP), mean transit time (MTT), time to arrival, peak height (PH), and/or area under the time-density curve (AUC). It will be recognized that such parameters may be determined by, for example, injection of contrast agent during an imaging sequence.

The method includes determining 106 a state of the vasculature using a machine-learning classifier applied to the one or more API maps. The machine-learning classifier may be, for example, a deep neural network (DNN) such as, for example, a convolutional neural network (CNN). The classifier is trained according to the vasculature state to be assessed. For example, the machine-learning classifier may be trained to determine an occlusion state of the vasculature. In another example, the classifier is trained to determine a reperfusion state of the vasculature. The classifier may be trained in known ways—e.g., using a training set of API maps and known vasculature states (examples of which are provided below). Applying the classifier to the one or more API maps may include extracting the features (e.g., hemodynamic parameter(s)) from the one or more API maps and using such features as inputs to the machine-learning classifier.

In some embodiments, the classifier may use ensemble networks. Such ensemble networks may be useful for classifying based on API maps from alternate views. For example, a CNN classifier may include a first network trained using anterior-posterior API maps, and a second network trained using lateral API maps. It should be noted that these are examples, and other standard and/or non-standard views may be used. The state of the vasculature is then determined using a combination of results from each network of the ensemble networks. The results of each network may be weighted by a network coefficient as further described below in Example 2.

The method 100 may further include providing 109 a vascular state assessment. For example, the assessment may be a predicted probability of success, a predicted probably of failure, etc., and may include a time component (predicted success at a time three months after the intervention). Vascular state (e.g., success of the intervention, failure, etc.) may be determined using any appropriate criteria. For example, vascular state may be assessed according to standard scoring systems, such as mTICI score, Raymond Roy score for coiling and the O'Kelly-Marotta grading system for flow diversion, and the like, and combinations thereof, as further described below. In some embodiments, the resulting vascular state assessment is provided 109 by displaying the result on a display.

In some embodiments, the one or more API maps are obtained 103 by generating 112 each API map from a DSA image sequence. In some embodiments, generating each API map includes temporally cropping 115 the DSA image sequence. For example, the DSA image sequence may be temporally cropped to only include frames where contrast is shown in the capillary phase (e.g., removing frames before and/or after the capillary phase, etc.) In other words, the DSA image sequence may be cropped to exclude some or all frames other than where contrast is shown in the capillary phase. In some embodiments, generating each API map includes spatially cropping 118 the DSA image sequence. For example, the DSA image sequence may be spatially cropped to remove some or all portions outside of a region of interest (e.g., extra-cranial regions, etc.)

In some embodiments, the API maps and/or the DSA images of the DSA image sequence may be segmented using a machine-learning classifier (i.e., an additional machine-learning classifier). Further description is provided below under the heading "Additional Aspect."

Injection Variability and/or Projection View Variability Reduction

Since the contrast injection rates during DSA acquisitions are dependent on the neurosurgeon, the present method may include normalizing the hemodynamic parameters to reduce injection variability. For example, pre-treatment and post-treatment values may be divided by the corresponding value at a pre-determined position on a main artery of the injection site. For example, in an IA, the pre-treatment and post-treatment values may be divided by the respective values measured at 2-3 cm proximal to the IA ostium.

A projection view may play an important role due to vessel foreshortening, where the contrast intensity in the angiogram correlates with the length of the x-ray pathway through structures. In order to reduce foreshortening error, a normalization may be applied, which assumes pre- and post-treatment views are identical. The one or more API maps may be corrected to account for C-arm position to reduce such foreshortening. For example, the post-treatment hemodynamic values may be divided by the corresponding pre-treatment values.

In some embodiments, a two-step normalization may be used. First, the pre- and post-treatment IA API values can be divided by the corresponding main artery API values measured at 2-3 cm proximal to the IA ostium. Next, the post-treatment normalized API values can be divided by the corresponding pre-treatment normalized ones.

Image Processing Apparatus

In another aspect, the present disclosure may be embodied as an image processing apparatus 10 (see FIG. 2). The apparatus 10 includes a memory 12 for storing API maps of a vasculature such as those described above. The memory can be, for example, a random-access memory (RAM) (e.g., a dynamic RAM, a static RAM), a flash memory, a removable memory, and/or so forth. In some instances, instructions associated with performing the operations described herein can be stored within the memory and/or a storage medium (which, in some embodiments, includes a database in which the instructions are stored) and the instructions are executed at a processor (below). In some embodiments, the one or more API maps may include a pre-treatment API map and a post-treatment API map.

A processor 20 is in electronic communication with the memory 12. The processor is programmed to perform any method described herein. For example, the processor may be programmed to determine a state of the vasculature based on the one or more API maps stored in the memory, and wherein the processor determines the state of the vasculature using a machine-learning classifier. The classifier may be trained to determine an occlusion state of a vasculature. The classifier may be trained to determine a reperfusion state of the vasculature. In some embodiments, the machine-learning classifier is a deep neural network (DNN), such as, for example, a convolutional neural network (CNN).

In some instances, the processor includes one or more modules and/or components. Each module/component executed by the processor can be any combination of hardware-based module/component (e.g., graphics processing unit (GPU), a field-programmable gate array (FPGA), an application specific integrated circuit (ASIC), a digital signal processor (DSP)), software-based module (e.g., a module of computer code stored in the memory and/or in the database, and/or executed at the processor), and/or a combination of hardware- and software-based modules. Each module/component executed by the processor is capable of performing one or more specific functions/operations as described herein. In some instances, the modules/components included and executed in the processor can be, for example, a process, application, virtual machine, and/or some other hardware or software module/component. The processor can be any suitable processor configured to run and/or execute those modules/components. The processor can be any suitable processing device configured to run and/or execute a set of instructions or code. For example, the processor can be a general purpose processor, a central processing unit (CPU), an accelerated processing unit (APU), a field-programmable gate array (FPGA), an application specific integrated circuit (ASIC), a digital signal processor (DSP), graphics processing unit (GPU), and/or the like. In a particular example, the processor may include a CPU and a GPU, wherein the GPU is configured as a machine-learning classifier.

In some embodiments, the machine-learning classifier of the processor may use ensemble networks. Such ensemble networks may be useful for classifying based on API maps from alternate views. For example, a CNN classifier may include a first network (of the ensemble networks) trained using anterior-posterior API maps, and a second network (of the ensemble networks) trained using lateral API maps. It should be noted that these are examples, and other standard and/or non-standard views may be used. The state of the vasculature is then determined using a combination of results from each network of the ensemble networks. The results of each network may be weighted by a network coefficient as further described below in Example 2.

In some embodiments, the processor 20 is programmed to obtain the one or more API maps and store the one or more API maps in the memory 12. For example, the processor may obtain the API maps from a communications interface (e.g., a network interface, etc.) In some embodiments, the processor obtains the one or more API maps by obtaining one or more DSA image sequences, and generating the one or more API maps from the one or more DSA image sequences. For example, each API map corresponds to a DSA image sequence. The processor may then store the generated one or more API maps in the memory.

In some embodiments, generating the one or more API maps may include one or more additional processing steps. For example, the processor may generate each API map by temporally cropping the DSA image sequence to only include frames where contrast is shown in a capillary phase. In another example, the processor generates each API map by spatially cropping each image of the DSA image sequence to remove portions outside a region of interest. In another example, the processor generates each API map by extracting a time density curve at each pixel of the DSA image sequence.

In some embodiments, the processor may be programmed to normalize the hemodynamic parameter to reduce injection variability. The processor may be programmed to correct the one or more API maps to account for C-arm position to reduce foreshortening error. The processor may be programmed to segment the one or more API maps using a DNN, such as a CNN (i.e., an additional classifier).

In some embodiments, the image processing apparatus further comprises an imaging sensor 30 in electronic communication with the processor 20. The processor may be further programmed to generate the one or more DSA image sequences using the imaging sensor.

The processor may be further programmed to provide a vascular state assessment. For example, the assessment may be a predicted probability of success, a predicted probably of failure, etc., and may include a time component (predicted success at a time three months after the intervention). Vascular state (e.g., success of the intervention, failure, etc.) may be determined using any appropriate criteria. For example, vascular state may be assessed according to standard scoring systems, such as mTICI score, Raymond Roy score for coiling and the O'Kelly-Marotta grading system for flow diversion, and the like, and combinations thereof, as further described below. In some embodiments, the resulting vascular state assessment is provided by displaying the result on a display. In some embodiments, the apparatus 10 includes a display 14 in electronic communication with the processor 20.

In another aspect, the present disclosure may be embodied as a non-transitory computer-readable medium having stored thereon a computer program for instructing a computer to perform any of the methods described herein. For example, the non-transitory medium may have instructions for obtaining one or more API maps of a vasculature, each API map of the one or more API maps encoding a (i.e., at least one) hemodynamic parameter; and determining a state of the vasculature based on the one or more API maps using a machine-learning classifier.

Further description is provided below with reference to certain exemplary embodiments. In the examples, the description is provided only to illustrate certain embodiments and applications of the present disclosure, and is not intended to be limiting.

Example 1

Intracranial Aneurysm Occlusion Prediction

Hemodynamic factors such as flow patterns, wall shear stress, and velocity play important roles in the initiation, growth, and rupture of intracranial aneurysms (IAs). The aim of endovascular treatments such as coil embolization and flow diversion are to occlude the IAs and reduce the risk of rupture by modifying the hemodynamics in the aneurysmal dome. These therapies reduce the mechanical stress exerted on the aneurysm wall, while catalyzing the endovascular clotting cascade. For IAs treated with a Pipeline Embolization Device (PED), occlusion may occur after several months, and minimum 6 months post-procedure follow-ups are required to assess the IA's occlusion status. For IAs treated with a PED, 21.8% remain partially to completely un-occluded and there is currently no accurate imaging-based diagnosis tool, which may predict IAs at risk of poor outcome.

Digital Subtraction Angiography (DSA) is the standard diagnostic imaging technique for the evaluation of IAs. DSAs are used to assess morphology and semi-quantitative intra-aneurysmal flow. There have been attempts to utilize this temporal information of contrast propagation for better diagnosis. The temporal and spatial contrast distribution may be used to perform Angiographic Parametric Imaging (API) by recording each pixel intensity in an image sequence. This method uses time density curves (TDCs) to calculate parameters such as Mean Transit Time (MTT), Time to Peak (TTP), Time to Arrival (TTA), Peak Height (PH) and Area Under the time density Curve (AUC). These parameters may be used to analyze IA flow aspects, or to evaluate flow changes due to treatment.

The main goals for this project were two-fold. First, we aimed to determine whether we could predict the minimum 6-month follow-up IA occlusion using API on pre- and post-intervention angiographic scans in conjunction with DNNs. Second, we aimed to investigate whether various normalization approaches applied to the API data can reduce errors due to injection variability and x-ray view foreshortening.

Embodiments of the presently-disclosed methods and systems may automatically extract flow parameters for pre- and post-treated aneurysms and predict the occlusion odds (for example, probability of occlusion at three months post-treatment) in real time, while the patient is still on the surgical table. Our initial results demonstrate the feasibility of training a machine learning tool to predict the outcomes using data from 200 patients with IAs undergoing endovascular treatment. An analysis was performed after the treatment with an endovascular device, coil, or flow diverter, which was then used as inputs for the tool. Aneurysm occlusion at 3-6 months was used as our classifier outcome. This was measured using a standard grading systems, the Raymond Roy score for coiling and the O'Kelly-Marotta grading system for flow diversion, and we formed a composite scale for outcomes categorization, as follows: (1) fully occluded or no flow inside the aneurysm, (2) remnant neck or minimal flow in the base of the aneurysm and (3) recurrence of the aneurysm or flow in the sac. Data was analyzed using the neural network and tool. The experimental embodiment of the neural network used five inputs: TTA, MTT, TTP, PH, and AUC. The data was augmented three fold, by assuming a normal distribution and creating new samples along that distribution by adding Gaussian noise to the mean of each of the API values. The augmented dataset was then split into two groups, 75% for training and 25% for testing. The network had three outputs for the aneurysm treatment outcome and demonstrated a predictive accuracy of 0.804. The maximum AUROC curve was 0.861 for flow diverters, indicating excellent performance.

Methods

Data Collection

The study schema used for the test embodiment is shown in FIG. 3. DSA scans from 180 patients with IAs treated only with a PED were collected for this study. All cases were collected from one center and the procedures were performed by four neurosurgeons. Only cases with a follow-up scan at least six months from the date of treatment were considered.

Due to image artifacts which prevented API analysis, 17 cases were excluded. In summary, 84.0% of cases had one aneurysm treated per intervention, 15.3% had two and 0.6% had three. In total, 190 IAs were used for the API analysis. The mean and median duration between treatment and follow-up were 9.8 and 8.0 months respectively. For each IA, DSA sequences were recorded at 3 time points: pre-treatment, immediately post-treatment, and follow-up. Of the 190 IAs considered, 171 were on the Internal Carotid Artery (ICA), of these, 3 were anterior choroidal, 53 cavernous, 8 cervical, 40 paraophtalmic, 31 supraclinoid (non-branch variants), 3 petro-cavernous, 1 terminus, 15 were on the posterior communicating artery (PComA), 17 were on the superior hypophyseal artery (SHA). Of the 19 IAs not on the ICA, 2 were on the anterior cerebral artery, 2 on the anterior communicating artery, 3 on the middle cerebral artery, 1 on the posterior cerebral artery, 5 on the posterior communicating artery, 6 were vertebra-basilar.

All angiograms in each patient study were observed retrospectively and pre- and post-treatment DSAs with best visualization of IAs were used to generate an API database. Occlusion outcome binary labels (occluded/un-occluded) were attained by neurosurgery attendings from the follow-up DSAs. API maps were generated from DSA sequences in an Angiographic Parametric Imaging software (Canon Medical Systems, Tustin, CA). For each case, expert users drew regions of interest over the aneurysm sac and the main artery to compute average MTT, TTP, PH, and AUC values. Inter-user variability was assessed by a single-tailed heteroscedastic t-test.

Occlusion Outcome Predictor Development

Individual API parameter use for IA occlusion prediction, without machine learning, limits the ability to use multiple parameters and their correlations. To address this multidimensional problem, we developed a DNN using a neural network library (Keras) to predict (classify) IA occlusion outcomes as a binary output: occluded or un-occluded. The DNN architecture design was an iterative process based on various network parameters optimization such as convergence, predictive accuracy, and receiver operating characteristic (ROC) metrics.

The final DNN architecture used contained three dense layers with 20, 60, and 20 output nodes in succession followed by a 20% dropout layer and a final dense layer with 2 nodes that made the prediction. A robust optimizer, Adadelta, that adapts learning rates based on a moving window of gradient updates was used as it automatically adjusts the learning rate as training progresses. DNNs were trained and tested on a single NVIDIA (Nvidia Corporation, Santa Clara CA) P2000 Graphics Processor Unit (GPU).

The DNN was evaluated using two quantitative metrics: classification accuracy and Receiver Operating Characteristic (ROC) curves. To test the network robustness and ensure that the results were not obtained due to a specific training-testing split, a Monte Carlo Cross Validation (MCCV) was conducted. Using this approach, the total dataset was randomly split twenty times into 70% (n=135) training and 30% (n=55) testing cohorts. Next, to prevent the DNN from overfitting, we used a previously-described method which implements Gaussian noise to augment the training and testing data sets separately, thus tripling the initial dataset. The process of augmentation was performed separately on the training and testing cohorts to avoid contribution of training cases in the testing cohort. Also, in order to set a benchmark and compare the performance of the DNN, we trained and a tested a Logistic Regression (LR) model on the relative augmented training and testing datasets.

Statistical Analysis

Subgroup analysis was conducted on the individual API parameters, (TTP, MTT, PH, and AUC), normalization method, and treatment status, as a function of occlusion outcome (occluded and un-occluded). Box and whisker plots were generated for each parameter and normalization method displaying the difference between occluded and un-occluded IAs. In addition, area under the ROC curve (AUROC) was computed for each API parameter as an individual predictor of IA occlusion outcome. P-values were calculated using a single-tailed heteroscedastic t-test to check if there was a statistically significant difference in the DNN performance between the three sub-groups (un-normalized, normalized, and relative). Furthermore, to determine normalization effect (normalizing for injection variability and foreshortening), sub-group analysis was carried on all data at all instances: no normalization (un-normalized set), arterial normalization (normalized set), and post-/pre-treatment normalization (relative set).

Results

API Data Collection and Inter Reader Variability

Figure 4:
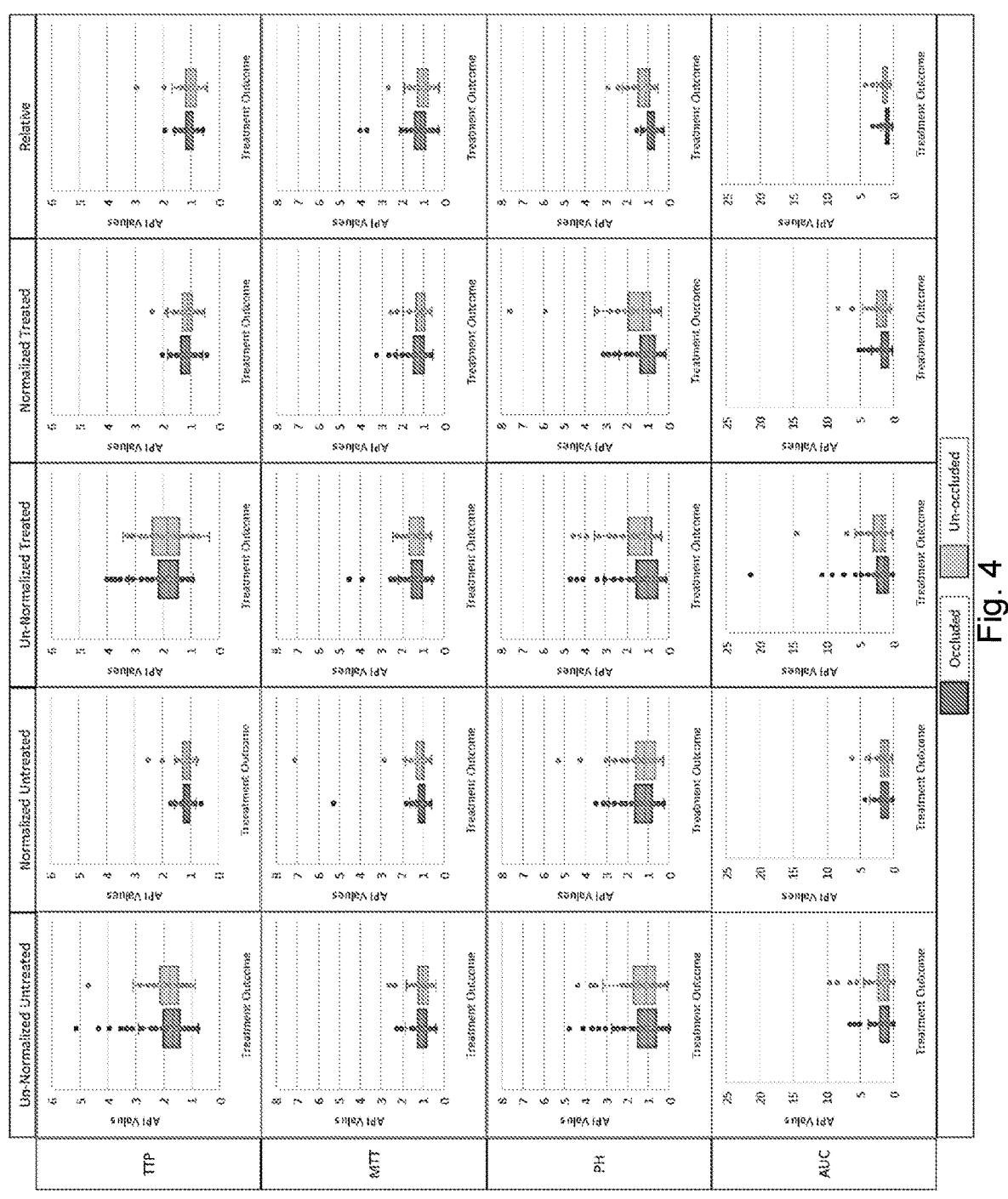
FIG. 4: Box and Whisker plots for each API parameter and normalization method of a non-limiting test embodiment are displayed. For each API parameter, within each normalization method, there is overlap and not much separation of values between occluded and un-occluded.

Raw API value analysis are displayed in the form of Box and Whisker plots for each API parameter and normalization method in FIG. 4. AUROCs for each API parameter as an individual IA occlusion predictor are displayed in Table 1. The p-values for the inter-reader variability for API parameter extraction from the aneurysm sac and arterial inlet among the three expert users were statistically not significant: 0.12, 0.16, and 0.46.

Upon observing the higher performance of PH individually as a predictor of IA occlusion outcome, the Youden index, which calculates the optimal classification threshold, was generated. For PH as a single occlusion outcome predictor, the optimal relative threshold was 0.87. At this value the diagnostic sensitivity and specificity for occlusion outcome was 0.92 and 0.57 respectively.

DNN Performance

Figure 5:
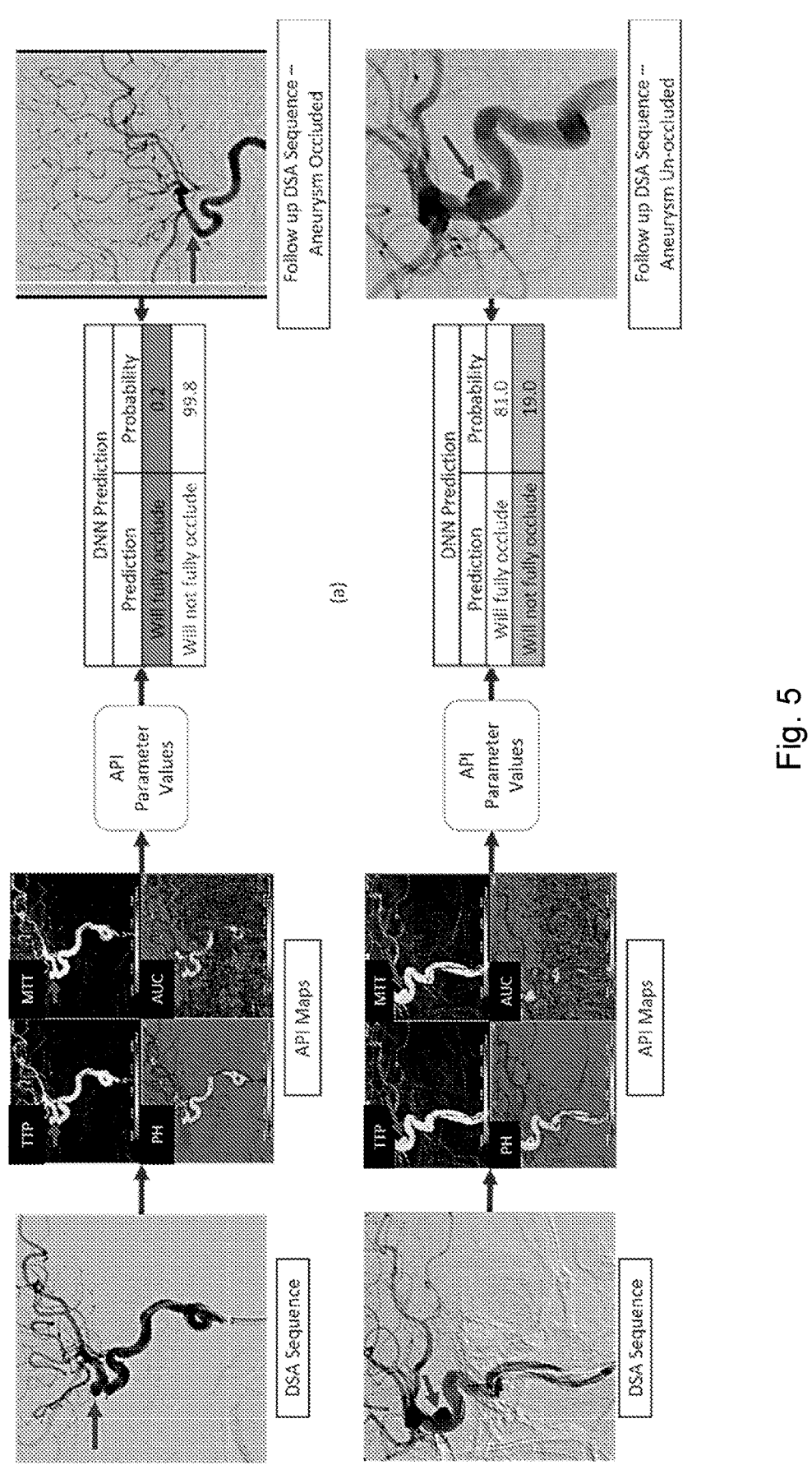
FIG. 5: The exemplary workflow used to test two specific cases is shown in (a) and (b). In both cases, the DSA sequence post-treatment is used to obtain API maps from which API parameter values are obtained. These values are run through the DNN which gives a probability of the IA occluding or not occluding. In case (a), the DNN predicted with 81% probability that the IA will occlude and that was confirmed by the follow up DSA sequence shown on the far right. In case (b), the DNN predicted with a 99.8% probability that the IA would not fully occlude and this was confirmed by the follow up DSA shown on the far right. Arrows depict locations of aneurysms (or location of where the aneurysms were before occlusion) on the DSA images and API maps.
Figure 6:
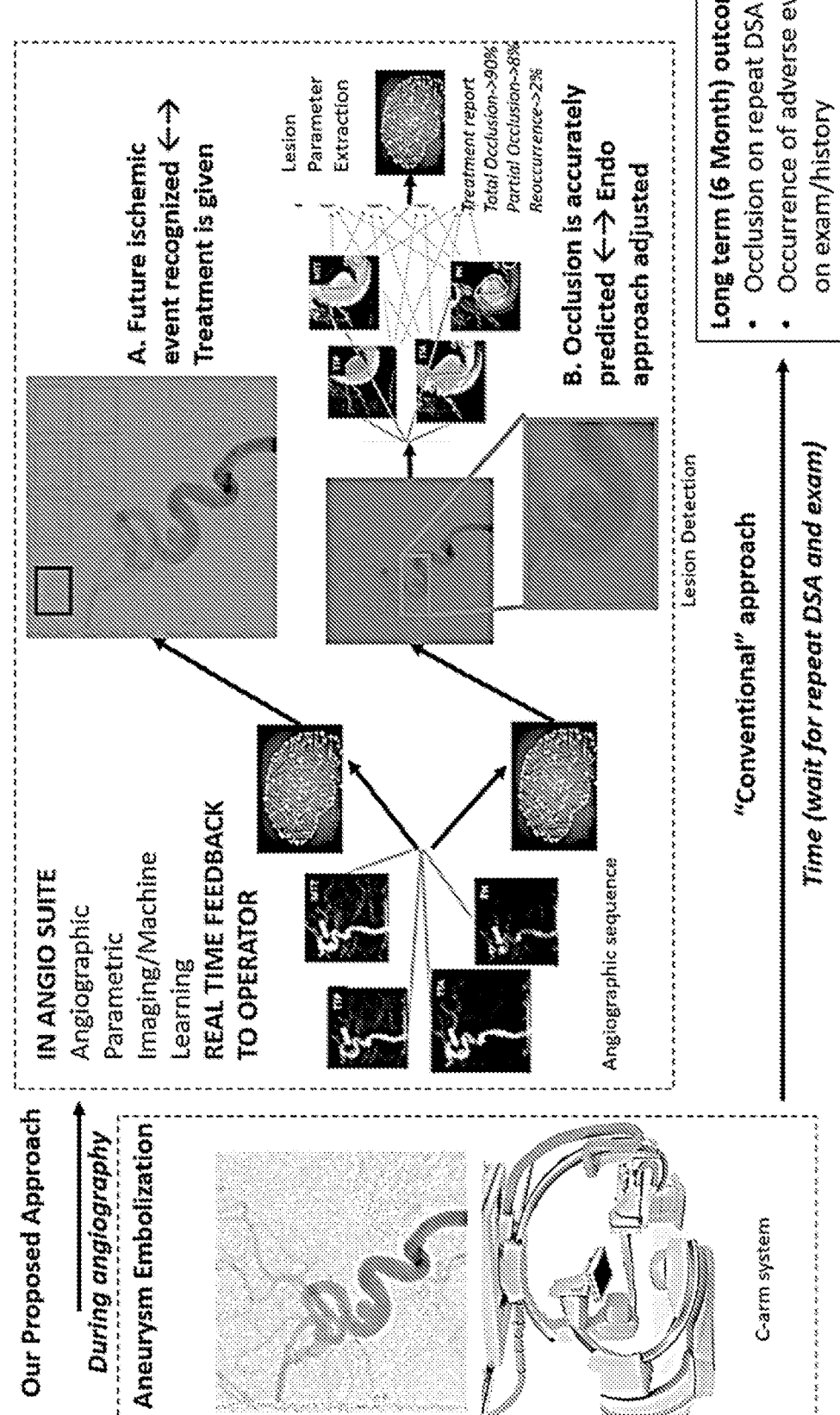
FIG. 6: Overview of an embodiment of a system for analyzing API data. In some embodiments of a system according to the present disclosure, the images, the C-arm position, and the x-ray acquisition parameters, can be directly interfaced in the system (though these components may or may not make up a part of such a system). Two AI modules may be in stand-by mode to process every sequence provided by the C-arm. The first module will analyze API data for ischemic event detection. The second module will assess the treatment of the vascular lesion being treated. This module may be disease specific (i.e., aneurysm, AVM, etc.) and may be able to identify automatically the lesion location, extract the API parameters in the lesion, and provide a prediction of the treatment outcome. This process may be implemented so as to have minimal or no disruption of the clinical workflow, while providing feedback (results) to the interventionalist in less than a second, after receiving the angiographic sequence.

The DNN required approximately 29 seconds to train and once trained, the DNN required 2 milliseconds to make a prediction on each case. DNN prediction examples on an occluded and un-occluded IA are shown in FIG. 5. The DNN predicted with a probability of 81% that the aneurysm in case (a) of FIG. 5 will occlude; this prediction matched the label as that aneurysm did occlude in the follow up. For the aneurysm in case (b) of FIG. 5, the DNN predicted with a probability of 99.8% that the aneurysm would not occlude which matched the label as that aneurysm did not occlude in the follow-up.

Average AUROCs, and average accuracies along with the standard deviations and 95% confidence intervals displaying DNN performance on the different normalization sub-groups and augmentation datasets are displayed in Table 1. P-values were calculated were calculated, using a single-tailed heteroscedastic t-test, between DNN performances on the three sub-groups (un-normalized, normalized, and relative). All p-values were in the range of $2.8 \times 10^{-3}$ to $3.1 \times 10^{-14}$ and thus below the statistically significant threshold of 0.05.

TABLE 1

Table 1: Performance of the DNN in predicting occlusion outcome of Intracranial Aneurysms in the form of average accuracies and average ROCAUCs along with their standard deviations and 95% confidence intervals is displayed. Results are displayed for each normalization sub-group as well as for each augmentation method. ROCAUCs predicting capability of each API parameter when used individually without a DNN are also displayed. The best performance is observed when both training and testing sets are augmented and the data undergoes a two-step normalization process (relative), the best results are shown in bold typeface.

| | | Accuracy (%) ± Standard Deviation (95% confidence interval (CI)) | AUROC ± Standard Deviation (95% CI) |
|---|---|---|---|
| Augmentation on training and testing cohorts | Un-Normalized | 62.5 ± 4.5 (60.5, 64.4) | 0.48 ± 0.09 (0.44, 0.52) |
| | Normalized | 70.8 ± 6.0 (68.2, 73.4) | 0.67 ± 0.13 (0.61, 0.73) |
| | Relative | 77.9 ± 3.9 (76.2, 79.6) | 0.77 ± 0.07 (0.74, 0.80) |
| | LR on relative | 76.7 ± 4.0 (74.9, 78.4) | 0.76 ± 0.06 (0.73, 0.79) |
| Augmentation only on training cohort | Un-Normalized | 64.5 ± 4.6 (62.5, 66.5) | 0.50 ± 0.08 (0.47, 0.53) |
| | Normalized | 68.2 ± 4.6 (66.2, 70.2) | 0.63 ± 0.09 (0.59, 0.67) |
| | Relative | 75.7 ± 4.3 (73.8, 77.6) | 0.69 ± 0.07 (0.66, 0.72) |
| No Augmentation | Un-Normalized | 65.8 ± 2.2 (64.8, 66.8) | 0.53 ± 0.08 (0.49, 0.57) |
| | Normalized | 67.5 ± 3.2 (66.1, 68.9) | 0.64 ± 0.08 (0.61, 0.67) |
| | Relative | 74.6 ± 3.5 (73.1, 76.1) | 0.73 ± 0.05 (0.71, 0.75) |
| Only TTP | Un-Normalized | N/A | 0.51 ± 0.08 (0.47, 0.55) |
| | Normalized | N/A | 0.43 ± 0.08 (0.39, 0.46) |
| | Relative | N/A | 0.44 ± 0.08 (0.41, 0.48) |

TABLE 1-continued

Table 1: Performance of the DNN in predicting occlusion outcome of Intracranial
Aneurysms in the form of average accuracies and average ROCAUCs along with their
standard deviations and 95% confidence intervals is displayed. Results are displayed
for each normalization sub-group as well as for each augmentation method. ROCAUCs
predicting capability of each API parameter when used individually without a
DNN are also displayed. The best performance is observed when both training and
testing sets are augmented and the data undergoes a two-step normalization process
(relative), the best results are shown in bold typeface.

|  |  | Accuracy (%) ± Standard Deviation (95% confidence interval (CI)) | AUROC ± Standard Deviation (95% CI) |
|---|---|---|---|
| Only MTT | Un-Normalized | N/A | 0.48 ± 0.07 (0.45, 0.51) |
|  | Normalized | N/A | 0.45 ± 0.07 (0.42, 0.48) |
|  | Relative | N/A | 0.43 ± 0.08 (0.39, 0.46) |
| Only PH | Un-Normalized | N/A | 0.58 ± 0.07 (0.55, 0.61) |
|  | Normalized | N/A | 0.66 ± 0.08 (0.62, 0.70) |
|  | Relative | N/A | 0.75 ± 0.06 (0.72, 0.77) |
| Only AUC | Un-Normalized | N/A | 0.57 ± 0.06 (0.54, 0.59) |
|  | Normalized | N/A | 0.66 ± 0.07 (0.63, 0.69) |
|  | Relative | N/A | 0.69 ± 0.06 (0.67, 0.72) |

Discussion

In this technical efficacy study, we established three main findings. First, we demonstrated that DNNs can use quantitative imaging information from API to predict IA occlusion immediately post-device deployment, instead of waiting a period of, for example, six months post-treatment. Second, we established that a normalization of API data to the vessel inlet as well as to the pre-treatment API values may be advantageous to improve performance by reducing injection variability and foreshortening. Third, it may be advantageous to use combinations of API (hemodynamic) parameters, rather than using an individual parameter, to make an accurate IA occlusion prediction.

In order to assess the ability of DNNs to predict occlusion of IAs, a DNN was trained and tested using API data derived from DSAs pre- and post-treatment with occlusion outcomes that were assigned by neurosurgeons from the follow-up scans. A 20-fold MCCV was conducted that allowed us to test the network robustness by providing average, standard deviation, and 95% confidence interval values for each evaluation metric. Results from the DNN on the un-normalized, normalized, and relative sub-groups (Table 1) were compared to test the technical feasibility of the normalization process employed. The DNN performed better on the relative sub-group than the normalized and un-normalized sub-groups by 7.1% and 15.5% in terms of average accuracy and 0.1 and 0.29 in terms of average AUROC respectively. The p-values between the three sub-groups were below the statistical significant threshold of 0.05, indicating a significant difference between performance on the un-normalized, normalized, and relative data. This indicates a significant advantage of using a two-step normalization process to predict the occlusion outcome of IAs using DNNs.

Using the analysis in FIG. 4, we confirmed that there was virtually no difference in the mean values between the occlusion outcomes for the un-normalized post-treatment API parameters. After the arterial normalization method, some separation was observed for PH and AUC, however this separation is not enough as seen by the performance of these parameters as individual predictors in Table 1. For the relative set following foreshortening correction, further mean value separation was observed, between occluded and un-occluded cohorts. In general, the AUROCs of each individual API parameter is less than the DNN AUROC (also displayed in Table 1) for each respective sub-group. The AUROC of PH as an individual predictor is higher than the other parameters, thus the Youden index indicating the optimal classification threshold and the sensitivity and specificity at that point were calculated. While the sensitivity had a high value of 0.92 at the optimal point, the specificity was only 0.57. Following this analysis, we concluded that for occlusion outcome prediction in IAs treated with PED, it may be advantageous to avoid using API parameters as single diagnostic indicators. Instead, it may be advantageous to implement DNNs which use the subtle correlations between these parameters to perform a more accurate prediction.

The DNN and LR models both achieved similar performances when trained and tested on the augmented relative dataset, this follow trends previously reported in other medical applications. There was no statistically significant advantage to using either of the two methods (p-value greater than 0.05). However simple LR models are known to have lower flexibility and require linearly separable data, increasing the number of input features would require greater model flexibility and less reliance on the presence of linearly separable data which is ideal for DNNs. Thus, while the performances are close, use of the DNN may prove to be more advantageous than an LR model if additional quantitative angiographic parameters are included.

In order to ensure no contribution of cases from the training set on the testing set, we conducted the augmentation after splitting the data into the training and testing sets. The difference in performance with and without augmentation on the training set was reported in Table 1. Better performance was observed when augmentation was done on both, training and testing cohorts. Performances were lower in the other two augmentation scenarios, which can be attributed to the number of cases in the testing set for those scenarios being one-third that of the first scenario. Once the dataset has been expanded, we may move away from augmenting the testing cohort and even the training cohort without negatively impacting the model predictive accuracy. The augmentation process in general may introduce DNN overfitting. To demonstrate absence of this in our study, we conducted a 20-fold MCCV which demonstrated small variability in the predictive capability of our network (Table 1).

One of the most impactful findings of this study was that a DNN may be advantageously used in angiographic suites in real time to predict the occlusion outcome immediately post device deployment (i.e., post intervention). Based on the resulting network prediction, the neurosurgeon may choose to adjust the treatment by deploying a second device or to perform appropriate follow-ups with the patient. There are three technical features which might improve the algorithm accuracy. First, the use of an auto-injector to standardize the rate of injections between neurosurgeons across different institutions would allow for a consistency in the database and would remove the need of arterial normalization. Second, the use of a higher frame rate than the current 3 frames per second during acquisition of the pre- and post-treatment DSAs would allow better-sampled TDCs to be obtained and thus increase the API accuracy. Third, maintaining the same C-arm angle during acquisition of the pre- and post-treatment sequences would prevent variability in the projection view, allowing for a more consistent relative API correction. These technical adjustments combined with an automatic aneurysm detection and radiomic feature extraction could provide a precise technology for decision support in the angiographic suites for the neurosurgeons.

Example 2

Ischemic Stroke Reperfusion Prediction

Patients with emergent large vessel occlusion (LVO) acute ischemic strokes (AIS) account for 24%-46% of all AIS cases. While there are many confounding factors, timely recanalization of such blockages is essential for optimal patient outcome. Mechanical thrombectomies (MT) aim at endovascular retrieval of clots to restore blood flow to ischemic territories. MTs are reported to have successful reperfusion rates between 75%-80% compared to 30% early recanalization rate when using intravenous thrombolysis with recombinant tissue-type plasminogen activators. Thus, MTs have markedly reduced severe disability and mortality compared to intravenous thrombolysis, and have been established as the standard care for LVO AISs.

Patients with LVOs undergo computed tomography (CT), CT angiogram (CTA) and CT perfusion (CTP) imaging to determine eligibility for the MT procedure, followed by the procedure itself. While pre-procedural AIS imaging has undergone major advancements, intra-procedural imaging still lags behind. Currently, intra-procedural MT success is assessed primarily by grading intracranial reperfusion using a cerebral digital subtraction angiogram (DSA). This is done using the thrombolysis in cerebral infarction (TICI) scale as proposed by Higashida et al, or the modified TICI scale (mTICI). mTICI grading systems has received criticism due to confusing internal inconsistencies as well as inclusion of bias due to grading being conducted solely through direct visual estimations of operators.

Intra-procedural assessment of such endovascular procedures could be improved using quantitative tools similar to CTP. Such implementation is limited due to the 2D nature of DSA and variability caused by hand injection of contrast. Angiographic parametric imaging (API) has been proposed as an alternative solution. This form of image analysis uses a DSA sequence to semi-quantitatively analyze blood flow through vasculature and angioarchitectures. Intensity at each pixel across the DSA sequence is measured, resulting in a time density curve (TDC) at each pixel. Parameterization of these TDCs enables extraction of various parameters such as mean transit time, time to peak, time to arrival, peak height (PH) and area under the TDC. This allows generation of API maps for each parameter which can be analyzed to understand nature of flow through different vessels and phases in DSAs. Each map encodes one hemodynamic parameter derived from each x-ray pathway, thus making maps less sensitive to subtle flow differences. This lack of sensitivity could be solved using a hybrid approach where hemodynamics encoded in API are combined with a data driven model.

A second exemplary application of the tool is the prediction of the ischemic stroke during thrombectomies. We developed a method combining angiography and machine learning to identify brain regions with poor blood perfusion in patients who presented with ischemic stroke. This approach employs a trained convolutional network that accepts as input four angiography API maps with the hemodynamic parameters of: Mean Transit Time, Time to Peak, Peak Height, and Area Under the Curve. Since in this case, we were studying ischemic stroke, patients had either large or medium artery occlusion and underwent mechanical thrombectomy. We used MRI (up to 48 hours post-procedure) as our gold standard for infarct core detection since using FLAIR imaging sequences the infarct core is very well-delineated from the surrounding tissues. We recorded the FLAIR data and synthesized various 3D projections for various views. The projection process implemented straightforward parallel beam voxel intensity counting. The projection that matched the unsubtracted x-ray angiographic view was selected by minimizing the differences between the two. Once the proper projection view was established, we used a standard co-registering algorithm based on bone features. Next, the infarcted tissue was manually segmented on the projection image and a mask was created.

For the proof of the concept, a deep neural network based on U-Net Architecture, was created such that the input to the network was comprised of four angiographic maps, MTT, TTP, PH, and AUC. The output of the network was the segmented co-registered projection of the infarct mask. We used 167 cases that were split in 75% training and 25% testing. The Receiver Operator Characteristic (ROC) was evaluated using ten-fold cross-validation. Training resulted in predictive accuracy over 80% and the area under the curve for the ROC was approximately 0.64. This tool can be used to monitor the brain re-perfusion status in real time while patient is still on the surgical table.

ADDITIONAL EXAMPLE

In this example, we present the use of CNNs with quantitative angiographic information from API to classify cerebral reperfusion during MT procedures. For the data driven classification, level of reperfusion was set using the mTICI scale. However, any other outcomes, including post-procedure MRI or neurologic evaluation, could be used.

Data Collection

Inclusion criteria for a test embodiment of the present exemplary application was any patient with an LVO undergoing a MT. For each patient, baseline, intraprocedural and post-MT DSAs were collected. Anteroposterior (AP) and lateral view DSAs were collected for every scan. Patients with posterior circulation occlusions were excluded. DSAs with image artifacts caused by patient motion during the scan, mainly in cases treated under conscious sedation, were also excluded from the study.

Acquisition of DSA sequences for all patients were conducted using Canon Infinix biplane systems (Canon Medical Systems Corporation, Otawara, Japan). DSAs were acquired at an average tube voltage of 84.3±5.0 kVp (average±standard deviation), tube current of 149.4±42.7 mA, pulse width of 84.0±12.1 ms and frame rate of 3 frames per second. Contrast used during acquisitions was iohexol (Omnipaque 350; GE Healthcare, Piscataway, New Jersey).

Figure 7:
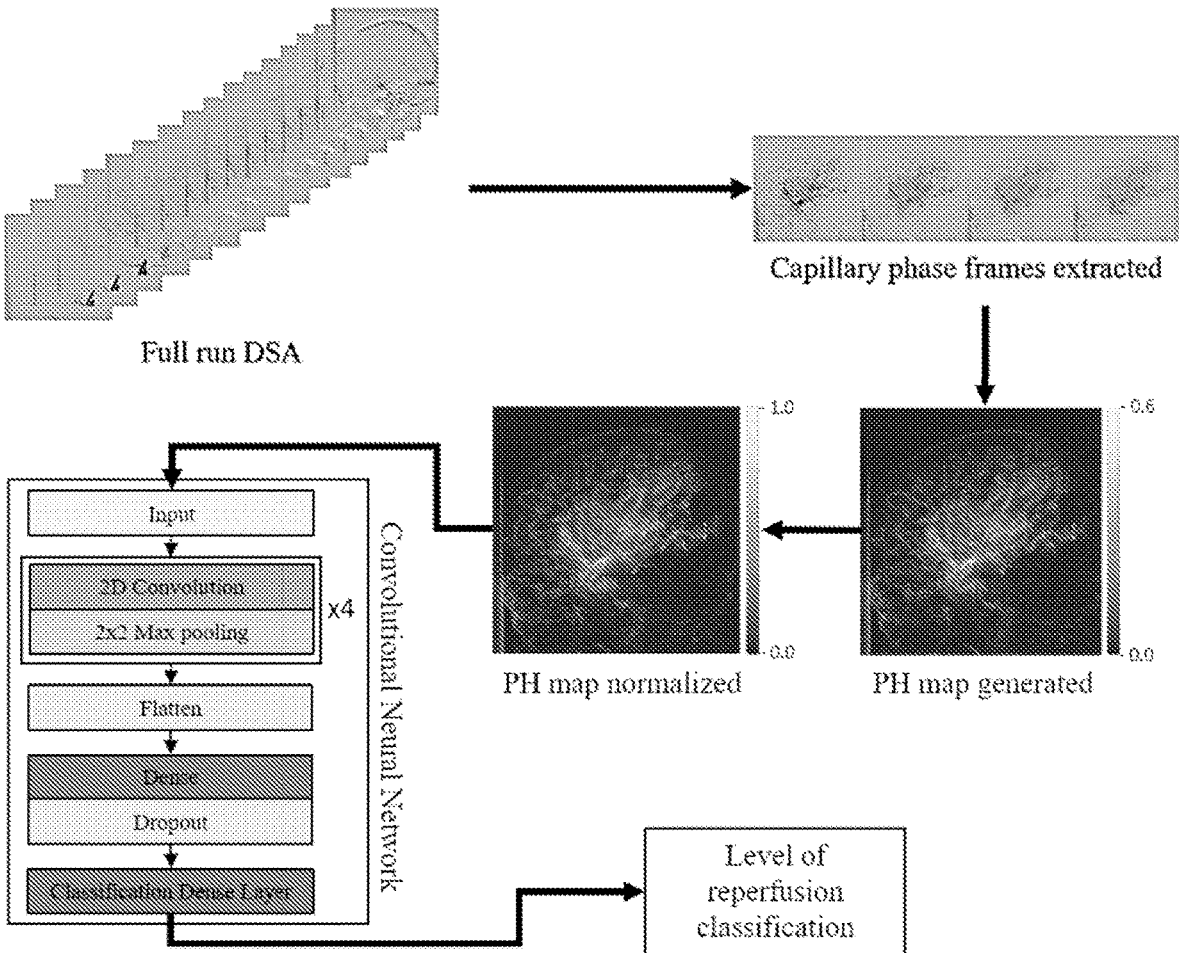
FIG. 7: A workflow of a test embodiment (DSA—Digital Subtraction Angiography, PH—Peak Height).

An exemplary method according to an embodiment of the present disclosure is displayed in FIG. 7. For each DSA included in analysis, an mTICI label was assigned by three experienced operators independently of each other. Operators were not involved in the procedure and were blinded to clinical outcomes. Grading was performed according to the following 6 categories: no perfusion (grade 0), partial perfusion beyond initial occlusion but not in distal arteries (grade 1), partial perfusion less than 50% (grade 2a), partial perfusion more than 50% but less than full (grade 2b), complete but delayed perfusion (grade 2c) and complete perfusion (grade 3). Cases with disagreements in mTICI labels were resolved by consensus decision. This was done to remove any bias in labels used for training the network.

API Map Generation

Evaluation of reperfusion with mTICI scores is done based on extent of tissue perfusion as represented by the capillary blush in DSAs. Each DSA was first cropped to only include frames where contrast was in the capillary phase. Thus, API maps did not contain any overlapping structures from arterial or venous phases.

TDCs were extracted at each pixel by tracking flow of contrast across frames in the cropped DSA sequence. PH maps were generated by calculating maximum value from TDCs at each pixel. For the purpose of this feasibility study, only PH maps were considered as it reflects maximum contrast intensity in each pixel across all frames and is thus most reflective of perfusion.

Since hand injection of contrast rather than an automatic injector was used for these emergent cases, injection parameters such as concentration, volume, and injection rate were highly heterogeneous between DSA acquisitions. To account for this variability, every pixel value in PH map was divided by the PH value in the main feeding artery. Thus, normalizing each map to contrast concentration in the respective inlet vessel.

Network Development

The CNN of the present test embodiment was developed using Keras to classify PH maps based on level of reperfusion. CNN architecture development was an iterative process based on optimization of metrics such as classification accuracy and receiver operating characteristic (ROC) curves. FIG. 7 shows an exemplary architecture of a CNN used in the present study. Optimizer used during training was Adam optimizer with an initial learning rate of $10^{-3}$. Loss function used was categorical cross-entropy. Keras callbacks were used to reduce the learning rate as training progressed and automatically terminate training as loss plateaued. In addition, class imbalance between classes was accommodated by implementing a balanced class weighting during training. Thus, the CNN balanced model layer weights to ensure equal penalization of under or overrepresented classes in the training set. CNNs were trained and tested on a single NVIDIA (Nvidia Corporation, Santa Clara CA) Tesla V100 graphics processing unit.

Following guidelines proposed by Radiology and in order to prevent overfitting of the network, we split the dataset with 70% (268 cases) reserved for training, 10% (39 cases) reserved as a validation set used for hyperparameter tuning during training, and 20% (77 cases) for testing. Hyperparameter tuning during training was done by tracking loss on the validation set. To test robustness of the network and ensure that results were not based on specific training-testing splits, a 20-fold Monte Carlo Cross Validation (MCCV) was conducted. This approach involves randomly splitting the total dataset into training and testing sets 20 times.

In order to combine information contained in both anterior-posterior (AP) and lateral PH maps, ensemble networks may be used. This method involves combination of predictions from multiple networks to give a final prediction by assigning a weight to predictions from each network. In an exemplary embodiment, one network was trained on AP PH maps and another network with the same architecture was trained on lateral PH maps. Weights to assign to predictions from individual networks were calculated using a differential evolution optimization algorithm implemented using SciPy. Once the weights were calculated, they were used to combine predictions from AP and lateral networks to give weighted ensembled predictions.

Ensembling outputs from individual networks may include assigning a weight to each network. In some embodiments, such weight values can be calculated using a differential evolution directed optimization process—a stochastic method to find the minimum of the loss function. This exemplary process does not use gradient methods, rather it searches large areas of candidate space. An example optimization was implemented using SciPy and used a known algorithm. The loss function used in the example optimization process was 1—Matthews correlation coefficient (MCC). MCC is used in machine learning models to evaluate quality of binary classifications. It has proven to be advantageous in the exemplary embodiment as it takes into account class imbalance and uses every factor in the confusion matrix (true positives, false positives, true negatives, and false negatives). In the example, once the weights were obtained, the output from the final dense layer of each network was multiplied by the weights for the network and these were the final outputs regarding the classification.

CNNs can automate outcome predictions and quantitative assessment of lesions such as intracranial aneurysms; however as a self-controlling minimization technique, they don't allow users to oversee which image features are most important and thus how to improve network predictions. We investigated the use of class activation maps (CAM) to visualize regions of PH maps that trigger the trained algorithm, thus lending insight to whether the CNN makes decisions based on flow or using some other portion of the image data which may not be as predictive of reperfusion. CAMs were generated using a method described by Zhou et al. They are obtained by taking outputs from the final convolutional layer and passing it through global average pooling layers. CAMs are heatmaps where regions of high intensity are regions considered important towards classification decisions by the network.

Statistical Analysis

The CNN was evaluated using five quantitative metrics including classification accuracy, ROC curves, AUROC, sensitivity, specificity, and MCC. Each of these metrics were averaged using results over the 20-fold MCCV. MCC is used in machine learning models to evaluate quality of binary classifications. It has proven to be advantageous as it takes in to account class imbalance and uses every factor in the confusion matrix (true positives, false positives, true negatives and false negatives).

Currently, when classifying intra-procedural DSAs as having sufficient or insufficient reperfusion to determine need for further treatment, clinicians either use a 2-outcome grouping where mTICI 0,1,2a is clinically insufficient reperfusion and mTICI 2b, 2c, 3 is sufficient reperfusion, or a 3-outcome grouping where mTICI 0,1,2a is insufficient reperfusion, mTICI 2c, 3 is sufficient reperfusion and mTICI 2b is either sufficient or insufficient reperfusion and the need for further treatment is decided based on other factors. Thus, in addition to a 2-outcome classification between mTICI 0,1,2a and mTICI 2b, 2c, 3, we also investigated a 3-outcome classification between mTICI 0,1,2a, mTICI 2b, and mTICI 2c, 3. In addition, sub group analysis was conducted for using AP and lateral view networks independently and, for using both views combined using the ensemble network. Two-tailed McNemar's p-test values were calculated in order to evaluate significance of any performance differences (p<0.05).

Results

We included 192 patients with 383 angiographic runs in our final analysis. Since angiographic runs from same Performance was also evaluated with ROC curves that are displayed in FIG. 10. Highest AUROC values were achieved when using ensembled networks. While in each plot, ROC curves for each sub-group are similar with overlap of standard deviations, McNemar's p-test values indicate significant advantage towards using lateral view over AP view (p-value <0.05) and towards using ensembled networks over AP or lateral view networks independently (p<0.05) for both, 2-outcome and 3-outcome classifications.

Class Activation Maps (CAMs)

Figure 9:
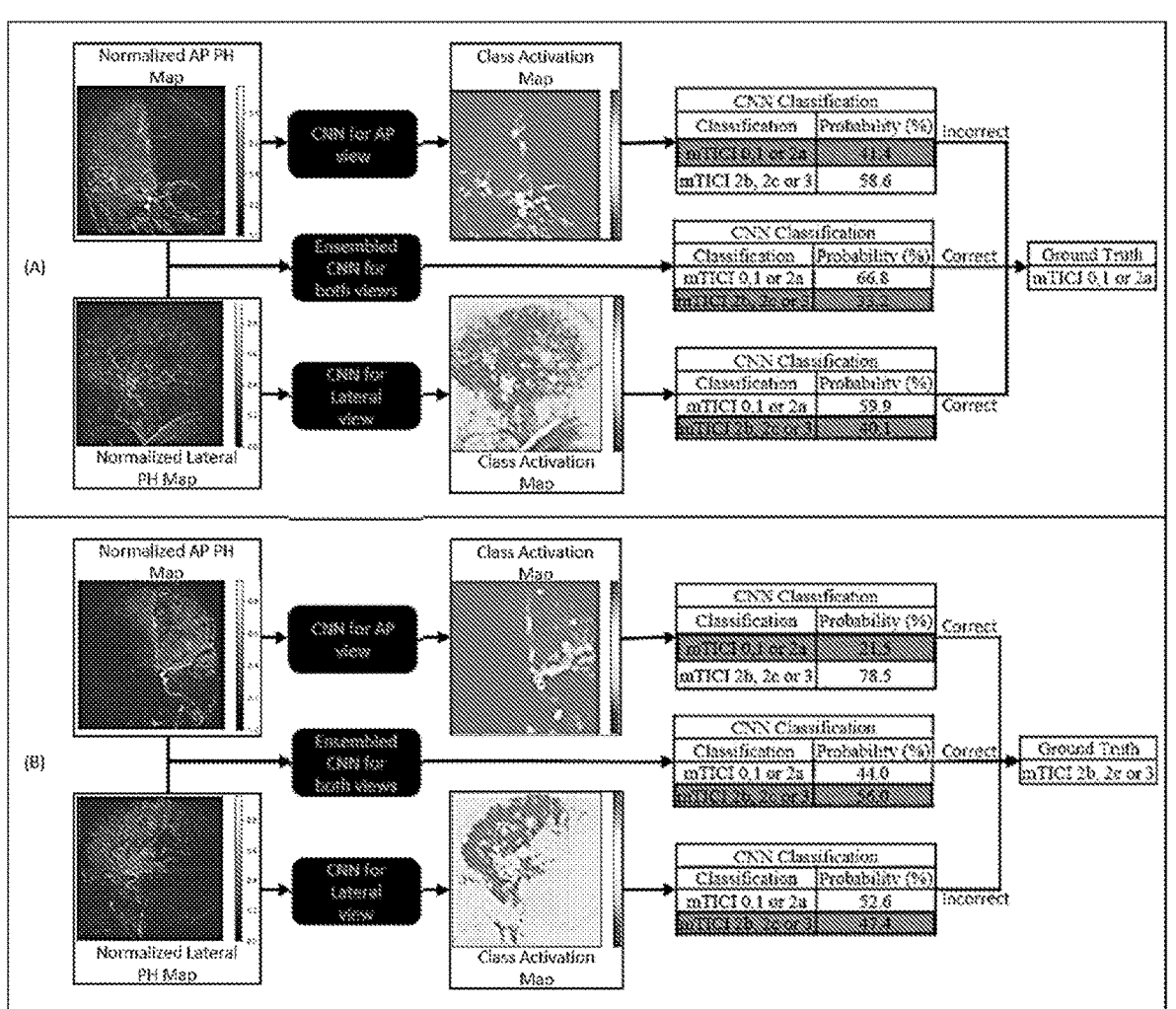
FIG. 9: (A) and (B) are two examples showing AP and lateral digital subtraction angiography (DSA) sequences, the normalized peak height (PH) maps generated from those sequences, the class activation maps (CAMs) as well as the classifications from the convolutional neural network (CNN) for each view and the ensembled CNN for both views. In (A), the AP view CNN incorrectly classifies the PH map as being mTICI 2b, 2c or 3 while the lateral view CNN and ensembled CNN both correctly classify the PH map as mTICI 0, 1 or 2a. In (B), the lateral view CNN incorrectly classifies the PH map as being mTICI 0, 1 or 2a while the AP view CNN and ensembled CNN both correctly classify the PH map as mTICI 2b, 2c or 3. This shows that misclassifications can occur when either AP or lateral views are used independently, however, when information from both views are combined using an ensemble network, the tool is able to correctly classify the DSA into the appropriate group. In each CNN classification table, the green highlight indicates the network classification. All the CAMs show that the activation occurs in the vessels with the larger vessels causing a higher activation.
Figure 10A:
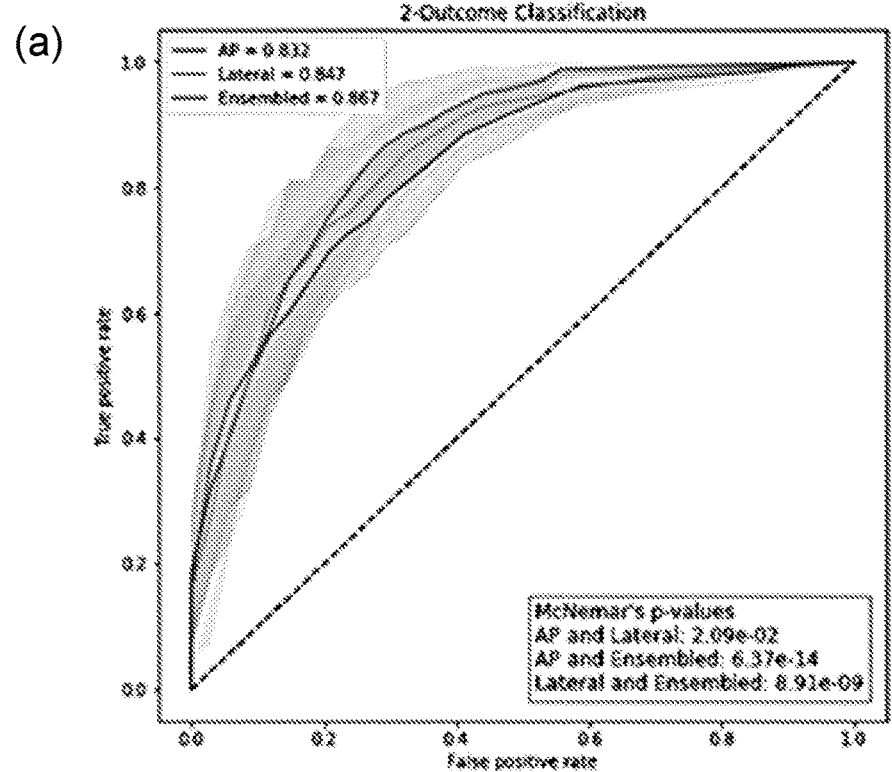
FIG. 10: Receiver Operating Characteristic (ROC) curves generated from the classifications of the Convolutional Neural Network (CNN). (a) depicts the ROC curves obtained for each sub-group when making a 2-class classification, (b) depicts the ROC curves for each sub-group for the mTICI 0,1,2a class when making a 3-class classification, (c) depicts the ROC curves for each sub-group for the mTICI 2b class when making a 3-class classification, and (d) depicts the ROC curves for each sub-group for the mTICI 2c, 3 class when making a 3-class classification. The shaded region around the ROC curve depicts the standard deviations at each point. High area under the receiver operating characteristic curve (AUROC) values and thin spread of standard deviations in (a) indicates the best performance is achieved when making a 2-class classification. In all four sub-plots, while the ROC curves and the standard deviations overlap between the three sub-groups, the McNemar's p-test values indicate significant improvement in performance when ensembled networks over AP and lateral view networks
Figure 10B:
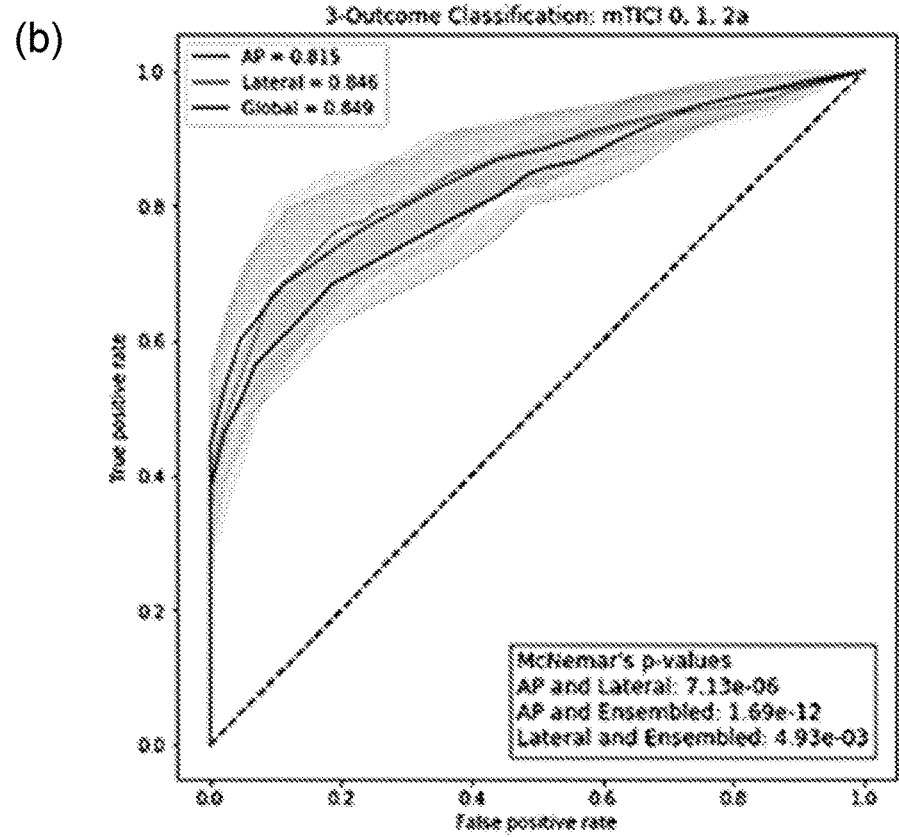
Figure 10C:
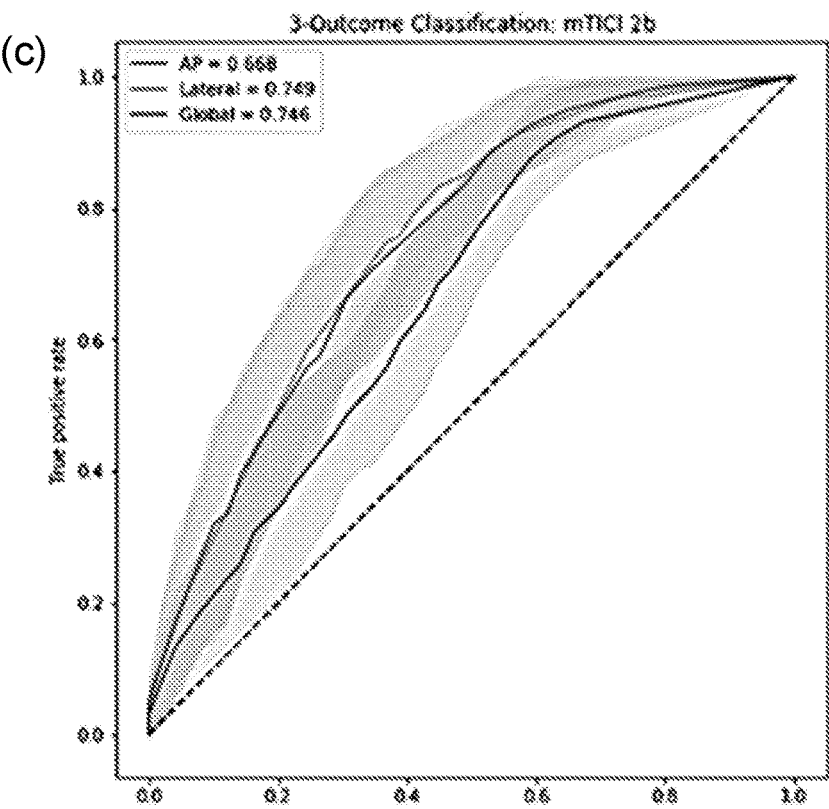
Figure 10D:
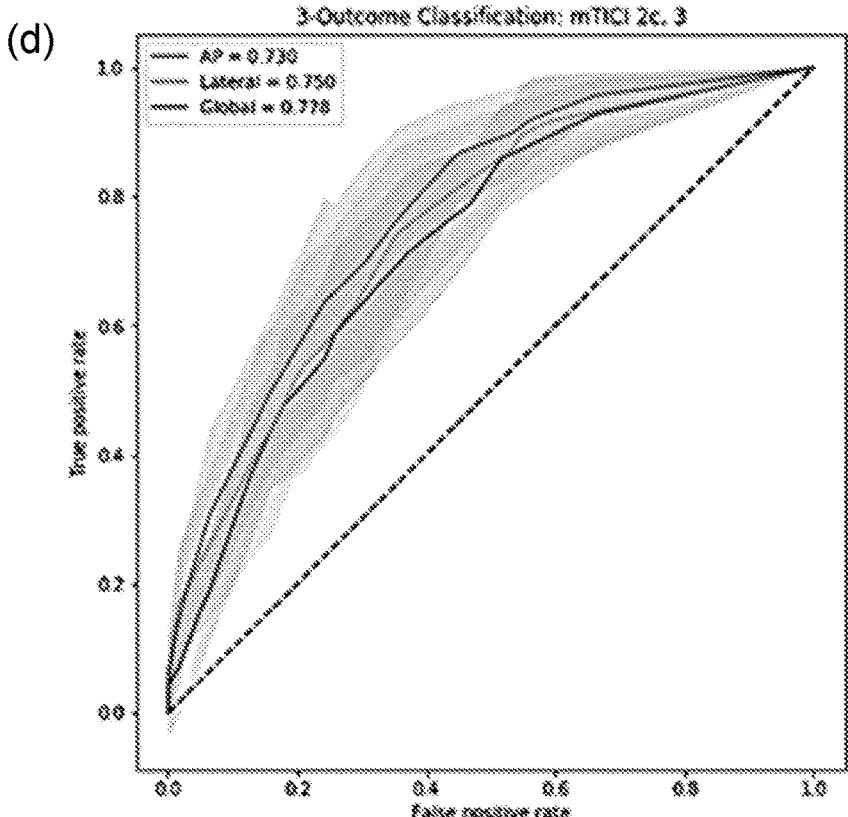

CAMs for two different cases were generated to visualize how the CNN makes its classifications, and are displayed in FIG. 9. The CAMs were able to display what regions of the PH maps were being used by the CNN to make the classification decision. The contrast in vasculature activated the network, with larger vessels having a higher activation. Thus, the network is looking at the presence of contrast and vasculature to make classification decisions. Internal carotid artery (ICA) terminus, middle cerebral artery (MCA) presence, and MCA territory, seemed to be greatest contributors towards classification decisions of the network.

TABLE 2

Performance of the convolutional neural network (CNN) in classifying DSAs based on their level of reperfusion based on the mTICI scale. Performance is displayed in the form of average accuracies, area under the receiver operating characteristic curves (AUROC), Matthews correlation coefficients (MCC), sensitivities, and specificities along with their standard deviations and 95% confidence intervals (CI). (A) shows the performance of the CNN when making a two-outcome classification (mTICI grade 0, 1, 2a versus mTICI grade 2b, 2c, 3) and (B) shows the performance when making a 3-outcome classification (mTICI grade 0, 1, 2a versus mTICI grade 2b versus mTICI grade 2c, 3). The 3-outcome classification requires a ROC curve for each outcome, thus there is an AUROC for each outcome in (B). The best results are in bold. The results indicate that best performance is achieved when making a 2-outcome classification using an ensembled network.

Figure 8:
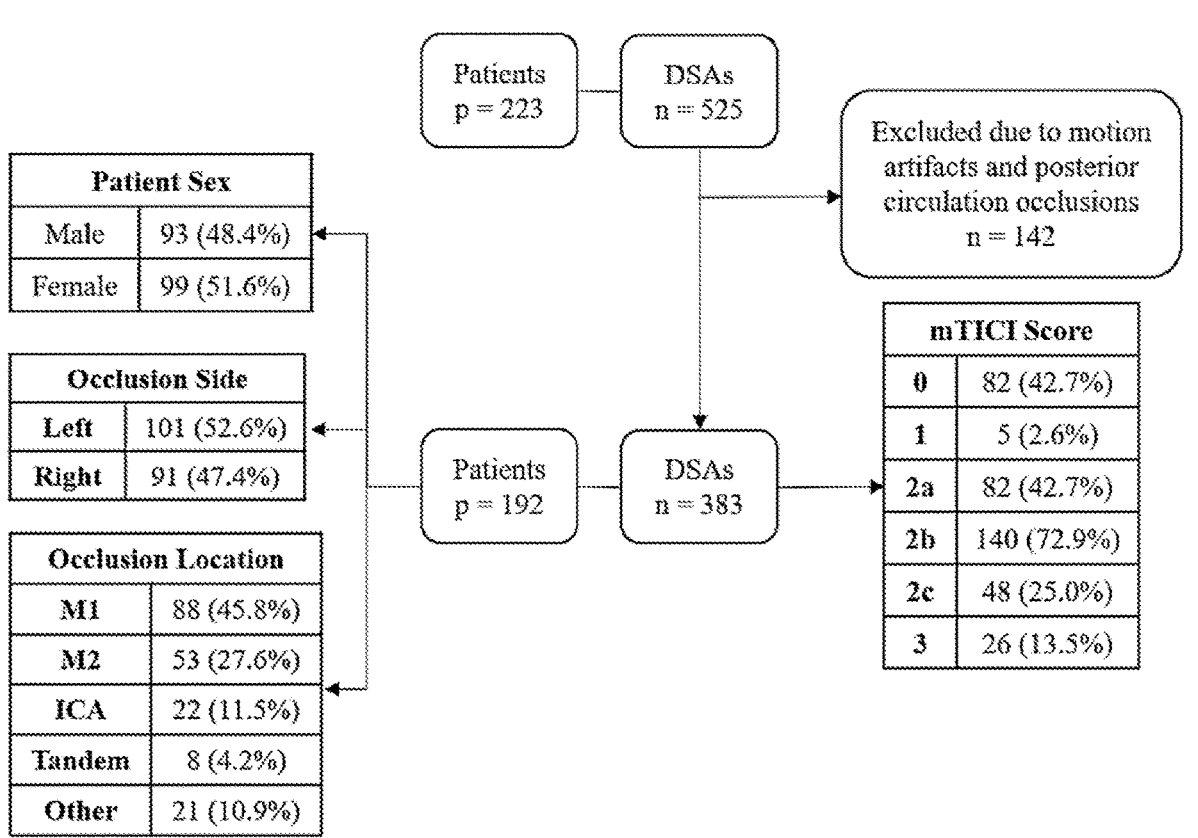
FIG. 8: Patient demographic information for patients in the test embodiment of FIG. 7. p refers to number of patients, n refers to number of DSAs (DSA—Digital Subtraction Angiography, ICA—Internal Carotid Artery).

| Metric | Only AP | Only Lateral | AP and Lateral Ensembled |
|---|---|---|---|
| 2 Class: mTICI 0, 1, 2a versus mTICI 2b, 2c, 3 | | | |
| Accuracy (%) | 74.2 ± 3.3 (72.8, 75.7) | 76.9 ± 5.9 (74.4, 79.5) | 81.0 ± 4.5 (79.0, 82.9) |
| AUROC | 0.83 ± 0.04 (0.81, 0.84) | 0.84 ± 0.05 (0.82, 0.87) | 0.86 ± 0.04 (0.84, 0.88) |
| MCC | 0.49 ± 0.07 (0.46, 0.52) | 0.54 ± 0.11 (0.49, 0.59) | 0.62 ± 0.09 (0.58, 0.66) |
| Sensitivity | 0.78 ± 0.1 (0.74, 0.83) | 0.84 ± 0.1 (0.79, 0.88) | 0.88 ± 0.08 (0.85, 0.92) |
| Specificity | 0.69 ± 0.12 (0.64, 0.75) | 0.68 ± 0.14 (0.62, 0.75) | 0.72 ± 0.11 (0.67, 0.76) |
| 3 Class: mTICI 0, 1, 2a versus mTICI 2b versus mTICI 2c, 3 | | | |
| Accuracy (%) | 56.0 ± 4.9 (53.9, 58.2) | 61.8 ± 4.1 (60, 63.6) | 64.0 ± 5.0 (62.0, 66.0) |
| AUROC 0 | 0.81 ± 0.04 (0.79, 0.83) | 0.84 ± 0.05 (0.82, 0.86) | 0.85 ± 0.04 (0.83, 0.87) |
| AUROC 1 | 0.67 ± 0.06 (0.64, 0.70) | 0.74 ± 0.06 (0.72, 0.77) | 0.74 ± 0.06 (0.71, 0.77) |
| AUROC 2 | 0.74 ± 0.05 (0.71, 0.76) | 0.75 ± 0.08 (0.72, 0.79) | 0.78 ± 0.06 (0.76, 0.81) |
| MCC | 0.30 ± 0.09 (0.26, 0.34) | 0.40 ± 0.07 (0.37, 0.43) | 0.43 ± 0.08 (0.40, 0.47) |
| Sensitivity | 0.66 ± 0.16 (0.59, 0.73) | 0.74 ± 0.08 (0.70, 0.77) | 0.80 ± 0.1 (0.75, 0.84) |
| Specificity | 0.73 ± 0.08 (0.69, 0.76) | 0.74 ± 0.08 (0.70, 0.77) | 0.76 ± 0.07 (0.73, 0.79) | patients were taken at different time points during MT procedures, they have different levels of reperfusion and can be considered as separate cases. Mean patient age was 68.75 years, initial NIH Stroke Score (NIHSS) was 12, post-procedure NIHSS was 4 and NIHSS shift was −7. Patient demographics, locations of LVOs and summary of mTICI scores are displayed in FIG. 8.

Network Performance

Average values for each evaluation metric along with their standard deviations and 95% confidence intervals are displayed in Table 2. Peak network performance was achieved when making a 2-outcome classification using an ensembled network that combined classifications from both, AP and lateral, view networks. While better performance was achieved in terms of accuracy, AUROC, MCC and sensitivity for 2-outcome classifications, better specificity was observed for 3-outcome classifications.

Discussion

An objective and unbiased assessment of reperfusion status after MT is advantageous for estimation of clinical prognosis and documentation for research purposes. In this study, we investigated technical feasibility of using a CNN with quantitative angiographic information to assess level of cerebral perfusion for patients undergoing a MT to treat an LVO AIS. We successfully classified PH maps generated from DSAs during an MT into 2-outcome categories (mTICI 0,1,2a and mTICI 2b, 2c, 3) or 3-outcome categories (mTICI 0,1,2a, mTICI 2b and mTICI 2c, 3). This indicates that data-driven models such as CNNs can be used to derive hemodynamic information encoded in API and make decisions regarding nature of cerebral blood flow.

Numerical results for five evaluation metrics used are displayed in Table 2, and ROC curves are displayed in FIG.

10. Peak performance was observed when making a 2-outcome classification using ensembled networks where information from both AP and lateral view networks were used to provide a final classification. This was observed considering high average values for each metric along with small standard deviations and tight confidence intervals. The numerical results, intersecting ROC curves, and overlapping standard deviations may indicate similar performance between each sub-group, however, McNemar's t-test p-values (p<0.05) indicate significant advantage to using ensembled networks over AP and lateral networks independently. In addition to commonly used evaluation metrics, we also calculated MCCs. Since MCC is an application of Pearson correlation coefficient, it follows the same patterns in terms of inferring strength of the correlation between classifications and ground truth. MCC values indicate strong positive relationships for 2-outcome classifications and moderate positive relationships for 3-outcome classifications. The performance of the network on 3-outcome classifications is lower for each sub-group, however it is still within an acceptable range given this is a feasibility study. The lower performance on 3-outcome classifications can be attributed to lower number of cases in each outcome (169 cases: 140 cases: 74 cases) compared to 2-outcome classification (169 cases: 214 cases) and to the increased complexity of the task of creating a finer classification. Increasing size of the dataset and increasing number of cases in each specific class will allow us to achieve higher performance on 3-outcome classifications.

In order to understand features from PH maps the CNN uses to make decisions, we generated CAMs. Two specific cases, including input PH maps, CAMs and final classification probabilities from the CNN for those cases were analyzed and displayed in FIG. 9. In both cases, the network was able to correctly classify the input PH map into mTICI 0,1,2a or mTICI 2b, 2c, 3 outcomes. In all four maps, we observed image regions that were activated were vessels, with higher activations in larger vessels. Thus, the network is making its decision based on image intensities in the vasculature. Using this method, we are able to analyze workings of CNNs instead of treating it simply as a black box without understanding mechanisms with which decisions are made. CAMs can also be used to optimize the input in order to improve performance of the network. In some embodiments, performance of the network may be improved by cropping regions outside the cranial cavity. For example, in FIG. 9, some activation is observed in extra-cranial regions, which should have no reperfusion classification information and may therefore be cropped. FIG. 9 also provides an example showing the potential advantage of using an ensembled network which combines information from both AP and lateral view networks. The figure shows misclassifications can occur when either AP or lateral view networks are used independently, however, when information from both networks are combined using an ensemble method, the PH map is correctly classified into the appropriate group.

The level of reperfusion was classified based on the mTICI scale which has its drawbacks. The method may be applied for other outcome scale such post-op MRI evaluation or a neurological evaluation, however these are not intra-procedurally acquired.

There are some limitations to this study described. First, we are only using 383 angiograms (268 for training, 39 for in-training hyperparameter tuning or validation, and 77 for testing) that were all collected from the same center. Thus, we are currently limited to demonstrating a technical feasibility study of using CNNs to assess level of reperfusion. Second, we are currently doing a 2- or 3-outcome classification and not a 6-outcome classification where the classification is a specific mTICI score. This is due to low number of cases per outcome (mTICI 0: 82, mTICI 1: 5, mTICI 2a: 82, mTICI 2b: 140, mTICI 2c: 48 and mTICI 3: 26) which leads to a decrease in performance, as seen when going from a 2- to 3-outcome classification. Third, we are currently not identifying location of LVOs, rather just the reperfusion status. Fourth, preprocessing methods such as cropping of DSAs to exclude arterial and venous phases, and identifying inlet vessels for normalization of PH maps were not automated in the study. It should be noted, however, that the scope of the presently-described methods and systems are not limited by the study. For example, the present method may be utilized for 6-outcome classifications or other outcome classifications. Also, some or all preprocessing steps (if any) may be automated and are considered in the scope of the present disclosure.

This study proves feasibility of using CNNs to extract encoded hemodynamic information from API by assessing level of reperfusion during an MT in patients with an LVO AIS. While this study provides neuro-interventionalists with a more robust tool to evaluate level of reperfusion during MTs rather than relying solely on subjective assessment of DSAs, it also proved feasibility of using CNNs with API maps and can thus be possibly used for other endovascular interventions.

Additional Aspect—Automatic Radiomic Feature Extraction Using Deep Learning for Angiographic Parametric Imaging of Intracranial Aneurysms The present techniques may automatically extract radiomic features using deep learning for angiographic parametric imaging of IAs. A typical angiographic parametric imaging computation at full resolution, currently 1024×1024 pixels, takes between 5 and 7 minutes to compute. User interaction with an interface to extract API parameters and insert them into a prediction algorithm might take another 2-3 minutes. Waiting around 10 minutes to make a surgical decision is not optimal for neuro endovascular procedures. To facilitate the process of extracting API values, we developed an artificial intelligence tool that automates segmentation (for example, aneurysm segmentation) and may extract contrast flow features within the sac. In a test embodiment, angiograms for 350 patients were collected and the aneurysm and surrounding vasculature were hand-contoured by an expert user, and a CNN was applied as further described herein.

Introduction

Digital subtraction angiography (DSA) is often used to evaluate the structural basis of neurovascular disease such as stenosis, arteriovenous malformations (AVMs), and intracranial aneurysms (IAs). In addition to the geometry and connectivity shown by standard DSA, angiographic parametric imaging (API) has helped clinicians evaluate the functional nature of these lesions. This may be useful in understanding natural history, predicting disease progression, or planning interventions. API uses contrast media flow characteristics in arteries and perfused tissue to synthesize a regional time density curve. By parametrization of the curve, features such as mean transit time and time to peak can be extracted. These parameters have been shown to relate to different physiological conditions such as AVMs, carotid stenting, and vasospasm.

Until recently, API was used only as a semi-qualitative tool, visualized as color maps overlain on DSA images, primarily due to an incomplete understanding of how the image features correlated with complex blood flow conditions and treatment outcomes. Studies have indicated that this tool may enable precise quantitative measurements and treatment assessments. The current workflow for targeted measurement of API features requires a user to manually outline the inlet region of the contrast media to the targeted vasculature and the IA. Manual contouring is not optimal in a clinical environment or for large-scale studies due to temporal inefficiencies of the process, but can be automated.

The use of deep learning networks, such as convolutional neural networks (CNNs), has gained popularity in numerous applications including facial recognition, language processing, drug discovery, and even the game of checkers. This is possible due to the CNN's ability to analyze connections and patterns between sets of image data at a dimension that humans cannot. With the advent of parallel processing and inexpensive graphical processing units, CNNs have been applied on a timescale that is more realistic to clinical applications. CNNs are capable of entire-image classification and more local classification processing such as bounding box detection. Further improvements that have increased the resolution to the individual pixel scale have opened the door to a pixel-by-pixel classification, essentially carrying out a semantic segmentation process with the network.

In the present example, a CNN trained with angiography data was used to automatically extract blood flow-related radiomic features. Such a process may increase the clinical usability of temporal angiographic data using API processing, and may allow its use in support of clinical decisions.

Methods

Image Collection

Figure 11:
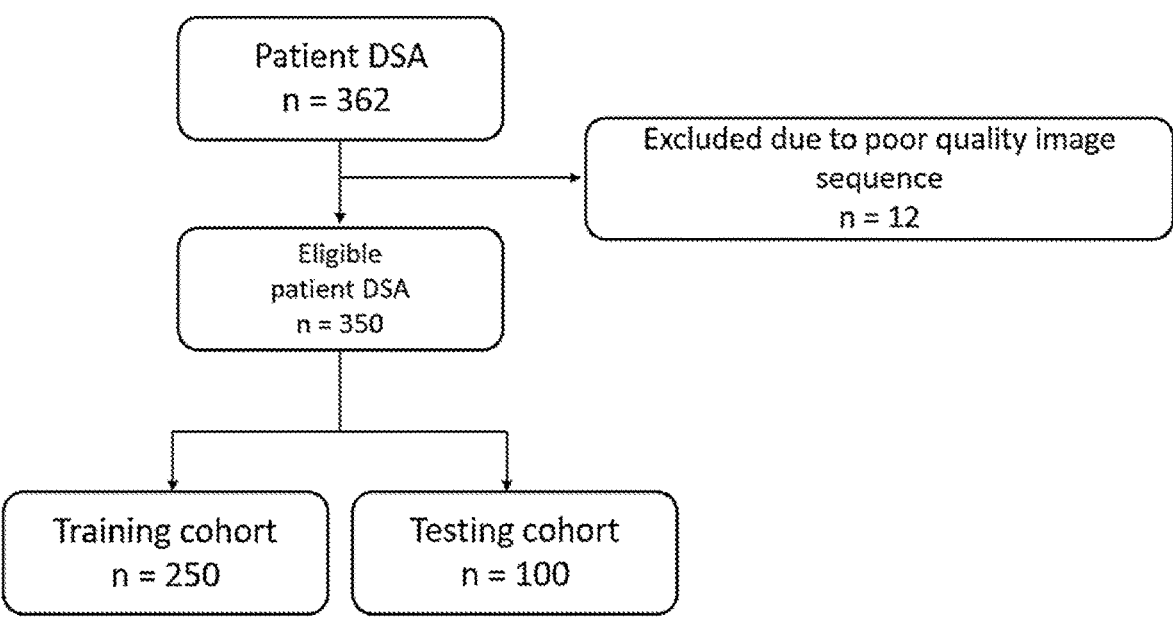
FIG. 11: Study inclusion flowchart schema. DSA, digital subtraction angiography.

The total inclusion flowchart schema for the present example is shown in FIG. 11. Inclusion criteria included image data of adult patients (between 18 and 90 years of age) scheduled for treatment for or treated for a saccular aneurysm with an endovascular coil at our institute's hospital. DSA image acquisition was carried out using a Canon Infinix-I Biplane angiography unit (Canon Medical Systems Corporation, Otawara, Japan) using iohexol contrast. After removing poor quality image sequences, 350 DSA acquisitions remained and were included in the present study, 192 prior to and 158 following aneurysm treatment. There were 313 aneurysms visible in the DSAs, 165 on the internal carotid artery (9 C2, 18 C4, 46 C5, 65 C6, and 27 C7), 98 on the anterior cerebral artery, 35 on the middle cerebral artery, 13 on the basilar artery, and 2 on the posterior cerebral artery. Note that there were acquisitions with multiple aneurysms. In such cases, the aneurysms were treated as separate in the same image acquisition. Due to the field of view or viewing angle selected, 45 DSAs did not have the aneurysm visible and were used as true-negative examples. This study tasked the network to identify aneurysms prior to treatment, aneurysms partially occluded due to intervention, and aneurysms completely occluded due to the coiling process.

Ground-Truth Label Creation

The IAs and surrounding vasculature were hand-contoured by users using a custom algorithm developed in the Laboratory Virtual Instrument Engineering Workbench (LabVIEW) (National Instruments, Austin, Texas, USA) programming environment. The users had a one year minimum exposure to evaluation of neurovascular angiograms at our institute. To reduce the background image noise, thus enhancing the vascular signal, the frames in the DSA sequences were averaged together when arteries and IAs were fully opacified to create a single frame. The averaged frame was passed through a two-dimensional median filter sized 3×3 pixels to attenuate background structure caused by motion artifacts. Then, an intensity threshold was applied to separate the background from the vasculature. Background pixels were assigned a value of 0; pixels within the vasculature class were assigned a value of 1. The aneurysm sac was separated from the surrounding vasculature using hand-contouring. Pixels within the aneurysm sac were assigned a value of 2. This entire process took approximately 2 minutes for each DSA sequence.

Data Augmentation

The 350 image frames were randomly split into two cohorts, 250 for training and 100 for testing. CNNs require large datasets to optimize the weights at each network layer. We used a data augmentation scheme created with Python (Python Software Foundation, Wilmington, Delaware, USA) to increase the size of our training dataset. The training and testing sets were expanded using a combination of rotations and zoom settings. Each averaged frame from the DSA sequences was rotated 90°, 180°, and 270° and zoomed in to 200% of its original size. The augmentation process expanded the training set to 1500 examples. The process of zooming in on regions of the image data during augmentation created new true-negative examples where no aneurysm was present, improving the trained network generalizability.

Machine Learning

The CNN architecture for the present non-limiting example was created within Keras. This architecture utilized a Visual Geometry Group-16 (VGG-16) encoder, two fully convolutional layers with rectified linear unit activation and 50% dropout, and a decoder consisting of transposed convolutional layers to up-sample the image data back to the original input image size. We tasked this network with a pixel-by-pixel semantic segmentation problem, where each pixel was classified as a member of one of three groups: background, vasculature, or aneurysm.

We ran modeling on an Nvidia Quadro K2200 GPU (Nvidia Corporation, Santa Clara, California, USA). Our network used the ADADELTA optimizer, an adaptive method for gradient descent which adapts the learning rate over time such that network learning continues even after many epochs. The summation of the Dice loss (the complement of the Dice similarity coefficient (DSC) and the binary cross-entropy) was used to compute the loss between the network's predicted mask and the ground-truth mask in the training cohort following each training epoch and was used to steer the gradient descent during training. Following the network weight optimization, the model was assessed using the testing cohort.

Network training relies on the ground-truth label accuracy for proper weight optimization. Two users created the training labels indicating that this process may be subject to interobserver variability. This variability was assessed by computing the percent overlap between hand-segmented aneurysm and vasculature contours in the 350 image frames by the two users.

Quantitative Analysis

Trained network predictive capability was assessed through multiple metrics. The area under the receiver operating characteristic curve (AUROC) was computed for the predicted masks using Python's scikit-learn version 0.20. The agreement between the predicted masks and the hand-contoured ground-truth labels was computed using the Jaccard index (JI) and the DSC to measure similarity between datasets. These metrics were computed and averaged for the aneurysm and vasculature predictions over the entire testing cohort.

To assess the similarities between the API features computed within the network predicted aneurysm region and those from the ground-truth aneurysm region in the API software, a mean percent difference over the testing cohort for each API feature was computed. Additionally, Pearson correlation coefficients were calculated to measure the correlation between the ground-truth API feature values and the network-extracted API feature values.

All analyses were repeated considering subgroupings of pre and post-coiled aneurysm cases to assess any network sensitivity to the type of input image data. Significance (p>0.05) of differences between subgroups was assessed with a one-tailed heteroscedastic t-test.

Results

The entire training process took approximately 24 hours for the network weights to converge to optimal values. Each example in the testing cohort was labeled in approximately 5 seconds by the network, and radiomic feature extraction using the API software within the aneurysm sac took an additional 5 seconds.

Segmentation Accuracy

The mean JI over the testing cohort was 0.823 (95% CI 0.783 to 0.863) for the IA and 0.737 (95% CI 0.682 to 0.792) for the vasculature. The mean DSC over the testing cohort was 0.903 (95% CI 0.867 to 0.937) for the IA and 0.849 (95% CI 0.811 to 0.887) for the vasculature. Considering only the pre-coiled cases in the testing cohort, the mean JI was 0.826 (95% CI 0.788 to 0.862) for the IA and 0.731 (95% CI 0.727 to 0.735) for the vasculature. Mean DSC over the pre-coiled cases in the testing cohort was 0.904 (95% CI 0.861 to 0.947) for the IA and 0.845 (95% CI 0.821 to 0.866) for the vasculature. Considering only the post-coiled cases in the testing cohort, the mean JI was 0.811 (95% CI 0.784 to 0.838) for the IA and 0.740 (95% CI 0.688 to 0.792) for the vasculature. Mean DSC over the post-coiled cases in the testing cohort was 0.891 (95% CI 0.869 to 0.913) for the IA and 0.851 (95% CI 0.811 to 0.891) for the vasculature. The differences in segmentation accuracy between the pre- and post-coiled examples in the testing cohort were not significant.

Diagnostic Accuracy

Figure 12:
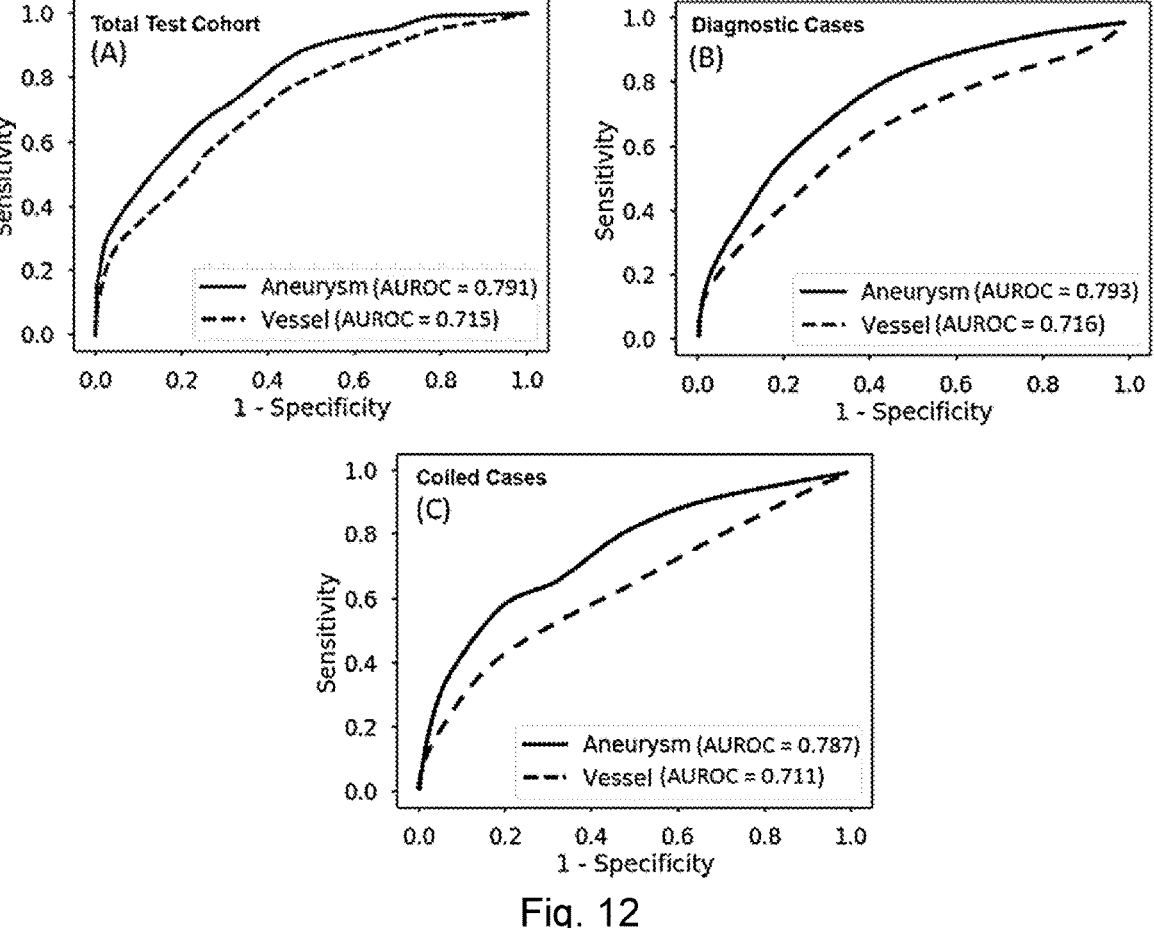
FIG. 12: (A) Receiver operating characteristic curves for the predicted segmentation of the aneurysm sac (solid line) and surrounding vasculature (dashed line) using the entire testing cohort. (B) Receiver operating characteristic curves for the predicted segmentation of the aneurysm sac and surrounding vasculature using the diagnostic cases in the testing cohort. (C) Receiver operating characteristic curves for the predicted segmentation of the aneurysm sac and surrounding vasculature using the coiled cases in the testing cohort. AUROC, area under the receiver operating characteristic curve.

The mean AUROC over the testing cohort was 0.791 (95% CI 0.740 to 0.817) for the IA and 0.715 (95% CI 0.678 to 0.733) for the vasculature. Considering only the pre-coiled cases in the testing cohort, the mean AUROC was 0.793 (95% CI 0.744 to 0.842) for the IA and 0.716 (95% CI 0.680 to 0.752) for the vasculature. Considering only the post-coiled cases in the testing cohort, the mean AUROC was 0.787 (95% CI 0.738 to 0.821) for the IA and 0.711 (95% CI 0.689 to 0.733) for the vasculature. The differences in the diagnostic accuracy between the pre- and post-coiled examples in the testing cohort were not significant. Receiver operating characteristic curves of the network's segmentation predictions using the entire testing cohort and the sub-groupings in the testing cohort are shown in FIG. 12.

Agreement Analysis

Figures 13, 14:
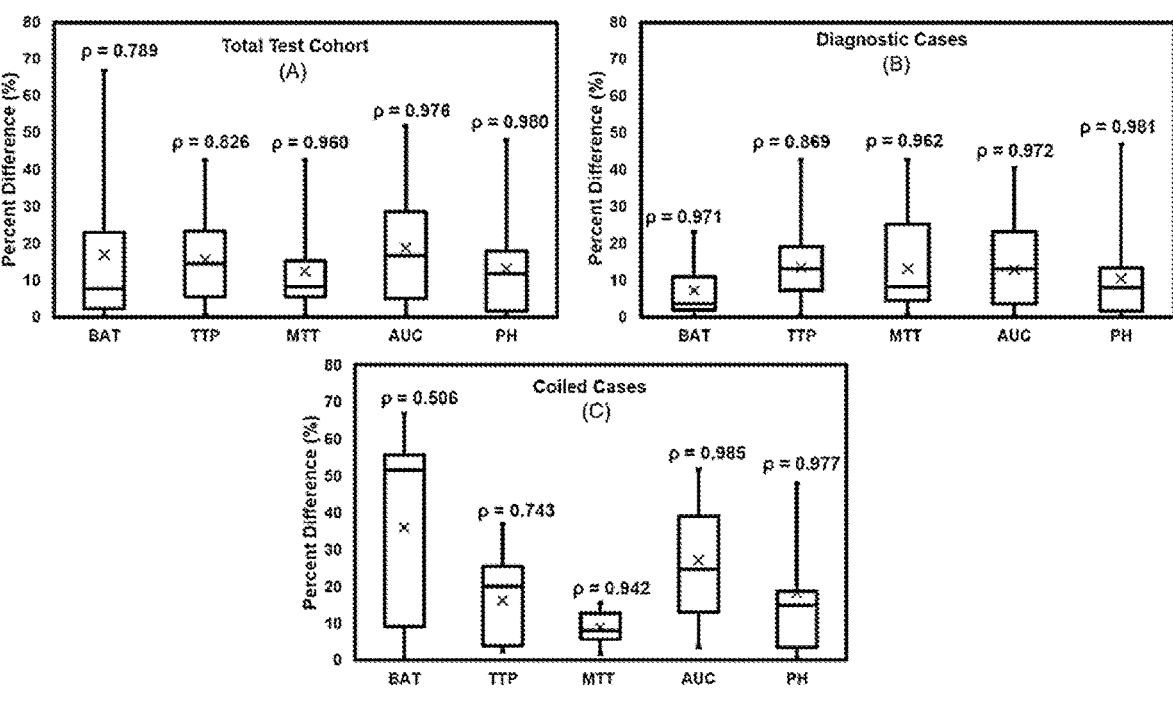
FIG. 13: (A) Box-and-whisker plots showing the mean percent difference between aneurysmal radiomic features computed within network IA predictions and those computed within human-contoured IA regions over the entire test cohort. X represents mean values for each feature. All five network-computed feature values had an average of <18% difference from those computed in the human-contoured regions. Pearson correlation coefficients ($\rho$) for each feature are shown. (B) Box-and-whisker plots showing the mean percent difference between aneurysmal radiomic features computed within network IA predictions and those computed within human-contoured IA regions considering just the diagnostic cases in the testing cohort. (C) Box-and-whisker-plots showing the mean percent difference between aneurysmal radiomic features computed within network IA predictions and those computed within human-contoured IA regions considering just the coiled cases in the testing cohort. AUC, area under the (time density) curve; BAT, bolus arrival time; IA, intracranial aneurysm; MTT, mean transit time; PH, peak height (of the time density curve); TTP, time to peak.
FIG. 14: (A) Single averaged digital subtraction angiography frame showing an intracranial aneurysm on the posterior communicating artery. (B) Corresponding angiographic parametric imaging feature map showing manual contour of aneurysm region by the human user. (C) Network segmentation overlaid onto image data in (A) with the aneurysm shown in blue and the vasculature shown in red, indicating agreement with the manually contoured mask shown in (B).

Qualitatively, the segmented masks for the aneurysm sac had notable overlap with the manual aneurysm labels, indicating that there should be good agreement expected between API values extracted within the two masks. Quantitatively, FIG. 13 shows box-and-whisker plots detailing the absolute average percent difference over the entire testing cohort, as well and when considering the pre- and post-coiled subgroups between five selected API features computed within the predicted aneurysm masks and API features computed within hand-contoured masks. The average percent differences were below 18% for all parameters when the entire testing cohort is considered. Also included on the box-and-whisker plots is the Pearson correlation coefficient between the API features extracted using the trained network-segmented masks and those of the manual user for all API features. Pearson correlation coefficients averaged over the features was 0.906 when the entire testing cohort is considered, indicating a linear correlation between the manually contoured masks and the network segmented masks.

Considering the diagnostic subgroup in the testing cohort, all API features had Pearson correlation coefficients greater than 0.86 indicating a linear correlation between the manually contoured masks and network segmented masks. The average percent differences were below 15% for all parameters. Considering the coiled subgroup in the testing cohort, all API features except bolus arrival time had Pearson correlation coefficients greater than 0.74, indicating a linear correlation between the manually contoured masks and network segmented masks for those features. There was a significant difference between the percent difference of the bolus arrival time API feature computed within the network and hand-contoured aneurysm regions considering the coiled and diagnostic examples in the test cohort. FIG. 4 shows qualitative agreement between the aneurysm network segmentation and the manual aneurysm segmentation.

Interobserver Variability

Over all image frames, the percent overlap between the ground-truth contours created by the two users was 95.5%, indicating little variability between the users during the label creation process.

Discussion

We presented a machine learning framework designed to automatically segment saccular IAs and surrounding vasculature from DSAs. The generated masks were used for a targeted API acquisition where radiomic features were extracted for quantitative lesion assessment. Pearson correlation coefficients indicated a strong association (p>0.78) between computed API feature values generated with the CNN or manual contouring. To our knowledge, this is one of the first studies to compare the capacity of a CNN-based algorithm to automatically extract API features from within an aneurysm sac against the current standard method of hand-contouring.

The use of VGG-16 architecture for the network encoder comes at the cost of computational time compared with shallower network architectures, necessitating a training time of approximately 24 hours for complete model weight convergence. When compared with other architectures for segmentation such as u-net that has over 31 million tunable parameters, the network used in this work has fewer parameters and can optimize the network weights more quickly and with fewer data.

Superior network performance was observed when segmenting the surrounding vasculature from the background in regions close to the aneurysm sac. As the contrast decreases towards the peripheral regions of the DSA frames, there is degraded segmentation accuracy. If the quantitative analysis of the segmentation accuracy were to be constrained to regions close to the aneurysm sac, the performance would improve.

When considering the diagnostic and coiled subgroups in the testing cohort, there was no significant difference in network segmentation accuracy for the aneurysm and vasculature classes indicating network independence to the input data in terms of treatment status. When comparing percent differences of specific API features between the diagnostic and coiled cases in the test cohort, only the bolus arrival time parameter had a significant increase in the percent difference. This parameter is prone to artifacts when devices such as catheters cause overestimation of bolus arrival time. If those regions are included in the aneurysm segmentation in either the network or hand-contoured labels, there will be a large mismatch in the estimation of bolus arrival time.

There were cases where the network missed a lesion that the human user found. This generally occurred with pre-coiled aneurysms <3 mm in size located off the internal carotid artery. Flattening the DSA sequences was suboptimal in the visualization of these aneurysms because it limited the contrast between them and the background. Moving forward, the use of class-activation maps to assess which aneurysm and vascular features the network finds most salient will be important for input data optimization.

The visualization of these features could be enhanced in relation to other less salient features in the image data which would allow better network detection and segmentation of the IA and surrounding vasculature.

Other metrics such as classification accuracy were not considered for this work due to the imbalanced size of the aneurysm sac class compared with the size of the vasculature and background class. The number of background pixels is large compared with the number of pixels within a typical aneurysm sac, leading to an artificially high accuracy measurement regardless of how the aneurysm sac was segmented.

This study had limitations. The amount of data used for the network training is small for such a deep network architecture when compared with other computer vision applications. To address this concern, we augmented the training dataset by a factor that was empirically set to six, which might imply network overfitting to the training data presented. The model's performance on the testing cohort suggests that the network does not suffer from overfitting. There are published works in the context of medical machine learning applications that have training datasets (n=200), (n=30), (n=376) on a similar scale to ours. Additionally, our network task uses image data that are not as diverse as other computer vision applications. Our image data are grayscale and have similar shape and intensities, reducing the task complexity. Another limitation is that the only type of aneurysms considered were saccular IAs and endovascular coiling was the only treatment method used. Other types of aneurysms (fusiform or dissecting) were not included in the study due to low incidence (but the present disclosure is intended to broadly include such aneurysm types and other treatment methods).

Our use of true-negative cases where the aneurysm was not visible may have introduced bias to the data, as these are not actual true-negative cases where there is no aneurysm at all. With this work, we did not attempt to create an aneurysm identifier that will work to diagnose the presence of an aneurysm. We aimed to use this tool when the presence of an aneurysm had been confirmed and treatment was being planned. We hope that such a tool will be useful in the context of aneurysm treatment planning, not necessarily diagnosis.

Our results indicate that the network performed non-inferiorly to a human user and required less manual input, which was more time efficient. The current standard method of performing API feature extraction can take up to 20 min on a 1024×1024 pixels image compared with approximately 10 seconds using the trained network. A clinical workflow may be used where, following the placement of an angiographic device, API can be carried out and the radiomic features computed using a trained network such as the one disclosed in this work. Next, the extracted API values can be passed to a clinical outcome predictor tool as demonstrated previously in the literature. This may provide the possibility for an informed decision by the neurosurgeon to revise the surgical procedure (e.g., add an extra coil) while the patient is still on the table or opt for closer observation. Overall, such a data-driven image data analysis using these radiomic features may lead to better occlusion rates and fewer complications following the procedure.

Conclusion

Our results show that a CNN can be trained to automatically segment saccular aneurysms (pre- or post-coiling) and surrounding vasculature from DSA images and that it is non-inferior at computing API features within the aneurysm sac compared with the standard method of hand-contouring. These trained CNN models may help to streamline clinical workflow and enable the use of more quantitative assessments of angiographic imaging methods

FURTHER EXAMPLES

In the following, various further examples of the present disclosure are described:

Example 1. A method for assessing a vasculature of an individual, including obtaining one or more angiographic parametric imaging (API) maps of the vasculature, wherein each API map of the one or more API maps encodes a hemodynamic parameter; and determining a state of the vasculature using a machine-learning classifier applied to the one or more API maps.

Example 2. The method of claim 1, wherein the machine-learning classifier is a convolutional neural network (CNN).

Example 3. The method of example 2, wherein the CNN includes ensemble networks.

Example 4. The method of example 3, wherein a first network of the ensemble networks is trained using anterior-posterior API maps and a second network of the ensemble networks is trained using lateral API maps, and the state of the vasculature is determined using a combination of results from each network of the ensemble networks.

Example 5. The method of example 4, wherein the result of each network is weighted by a network coefficient.

Example 6. The method of any one of examples 1-5, wherein the machine-learning classifier is trained to determine an occlusion state of the vasculature.

Example 7. The method of any one of examples 1-5, wherein the machine-learning classifier is trained to determine a reperfusion state of the vasculature.

Example 8. The method of any one of examples 1-7, wherein the hemodynamic parameter is one or more of time to peak (TTP), mean transit time (MTT), time to arrival, peak height (PH), and/or area under the time-density curve (AUC).

Example 9. The method of any one of examples 1-8, further having normalizing the hemodynamic parameter to reduce injection variability.

Example 10. The method of any one of examples 1-9, further having correcting the one or more API maps to account for C-arm position to reduce foreshortening error.

Example 11. The method of any one of examples 1-10, wherein the received one or more API maps include a pre-treatment API map and a post-treatment API map.

Example 12. The method of example 11, further having dividing the hemodynamic parameter of the post-treatment API map by the corresponding hemodynamic parameter of the pre-treatment normalized API map.

Example 13. The method of any one of examples 1-12, wherein the one or more API maps are obtained by generating each API map from a digital subtraction angiography (DSA) image sequence of the vasculature.

Example 14. The method of example 13, wherein generating each API map includes temporally cropping the DSA image sequence to only include frames where contrast is shown in the capillary phase.

Example 15. The method of any one of examples 13-14, wherein generating each API map includes spatially cropping the DSA image sequence to remove portions outside a region of interest.

Example 16. The method of any one of examples 13-15, wherein generating each API map includes extracting a time density curve at each pixel of the DSA image sequence.

Example 17. The method of any one of examples 1-16, further having segmenting the one or more API maps using a CNN.

Example 18. An image processing apparatus, including a memory for storing one or more angiographic parameter imaging (API) maps of a vasculature, wherein each API map of the one or more API maps encodes a hemodynamic parameter; and a processor in electronic communication with the memory, and wherein the process is programmed to determine a state of the vasculature based on the one or more API maps stored in the memory, and wherein the processor determines the state of the vasculature using a machine-learning classifier.

Example 19. The image processing apparatus of example 18, wherein the processor is further programmed to obtain the one or more API maps and store the one or more API maps in the memory.

Example 20. The image processing apparatus of example 18, wherein the processor is further programmed to obtain one or more digital subtraction angiography (DSA) image sequences; generate one or more API maps from the one or more DSA image sequences, wherein each API map corresponds to a DSA image sequence; and store the generated one or more API maps in the memory.

Example 21. The image processing apparatus of any one of examples 18-20, wherein the processor generates each API map by temporally cropping the DSA image sequence to only include frames where contrast is shown in a capillary phase.

Example 22. The image processing apparatus of any one of examples 20-21, wherein the processor generates each API map by spatially cropping each image of the DSA image sequence to remove portions outside a region of interest.

Example 23. The image processing apparatus of any one of examples 20-22, wherein the processor generates each API map by extracting a time density curve at each pixel of the DSA image sequence.

Example 24. The image processing apparatus of any one of examples 20-23, further having an imaging sensor in electronic communication with the processor, and wherein the processor is further programmed to generate the one or more DSA image sequences using the imaging sensor.

Example 25. The image processing apparatus of any one of examples 18-24, wherein the machine-learning classifier of the processor is trained to determine an occlusion state of a vasculature.

Example 26. The image processing apparatus of any one of examples 18-25, wherein the machine-learning classifier of the processor is trained to determine a reperfusion state of the vasculature.

Example 27. The image processing apparatus of any one of examples 18-26, wherein the machine-learning classifier of the processor is a convolutional neural network (CNN).

Example 28. The image processing apparatus of example 27, wherein the CNN includes ensemble networks.

Example 29. The image processing apparatus of example 28, wherein a first network of the ensemble networks is trained using anterior-posterior API maps and a second network of the ensemble networks is trained using lateral API maps, and the processor is programmed to determine the state of the vasculature using a combination of results from each network of the ensemble networks.

Example 30. The image processing apparatus of any one of examples 28-29, wherein the processor is further programmed to weight a result of each network by a network coefficient.

Example 31. The image processing apparatus of any one of examples 18-30, wherein the hemodynamic parameter is one or more of time to peak (TTP), mean transit time (MTT), time to arrival, peak height (PH), and/or area under the time-density curve (AUC).

Example 32. The image processing apparatus of any one of examples 18-31, wherein the processor is further programmed to normalize the hemodynamic parameter to reduce injection variability.

Example 33. The image processing apparatus of any one of examples 18-32, wherein the processor is further programmed to correct the one or more API maps to account for C-arm position to reduce foreshortening error.

Example 34. The image processing apparatus of any one of examples 18-33, wherein the one or more API maps include a pre-treatment API map and a post-treatment API map.

Example 35. The image processing apparatus of any one of examples 18-34, wherein the processor is further programmed to segment the one or more API maps using a CNN.

Example 36. A non-transitory computer-readable storage medium having instructions thereon to cause a processor to perform a method according to any one of examples 1-17.

Example 37. An image processing apparatus, comprising a processor programmed to perform a method according to any one of examples 1-17.

Although the present disclosure has been described with respect to one or more particular embodiments, it will be understood that other embodiments of the present disclosure may be made without departing from the spirit and scope of the present disclosure.

What is claimed is:

1. A method for assessing a vasculature of an individual, comprising:

obtaining one or more angiographic parametric imaging (API) maps of the vasculature, wherein each API map of the one or more API maps encodes a hemodynamic parameter, and wherein the hemodynamic parameter comprises one or more of time to peak (TTP) mean transit time (MTT), time to arrival, peak height (PH), and/or area under the time-density curve (AUC);

determining a state of the vasculature using a machine-learning classifier applied to the one or more API maps, wherein the machine-learning classifier is trained to determine a reperfusion state of the vasculature, an occlusion state of the vasculature, or both; and displaying, in real-time during an endovascular procedure, a vasculature state assessment based on the determined state of the vasculature to provide feedback for adjusting the endovascular procedure, wherein the vasculature state assessment includes a probability of achieving a relevant therapeutic outcome as defined by established clinical standards.

2. The method of claim 1, wherein the machine-learning classifier is a convolutional neural network (CNN).

3. The method of claim 2, wherein the CNN comprises ensemble networks.

4. The method of claim 3, wherein a first network of the ensemble networks is trained using anterior-posterior API maps and a second network of the ensemble networks is trained using lateral API maps, and the state of the vasculature is determined using a combination of results from each network of the ensemble networks.

5. The method of claim 4, wherein the result of each network is weighted by a network coefficient.

6. The method of claim 1, wherein the machine-learning classifier is trained to determine an occlusion state of the vasculature.

7. The method of claim 1, wherein the machine-learning classifier is trained to determine a reperfusion state of the vasculature.

8. The method of claim 1, further comprising normalizing the hemodynamic parameter to reduce injection variability.

9. The method of claim 1, further comprising correcting the one or more API maps to account for C-arm position to reduce foreshortening error.

10. The method of claim 1, wherein the received one or more API maps comprise a pre-treatment API map and a post-treatment API map.

11. The method of claim 10, further comprising dividing the hemodynamic parameter of the post-treatment API map by the corresponding hemodynamic parameter of the pre-treatment normalized API map.

12. The method of claim 1, wherein the one or more API maps are obtained by generating each API map from a digital subtraction angiography (DSA) image sequence of the vasculature.

13. The method of claim 12, wherein generating each API map comprises temporally cropping the DSA image sequence to only include frames where contrast is shown in the capillary phase.

14. The method of claim 12, wherein generating each API map comprises spatially cropping the DSA image sequence to remove portions outside a region of interest.

15. The method of claim 12, wherein generating each API map comprises extracting a time density curve at each pixel of the DSA image sequence.

16. The method of claim 1, further comprising segmenting the one or more API maps using a CNN.

17. A non-transitory computer-readable storage medium having instructions thereon to cause a processor to perform a method according to any one of claims 1-16.

18. An image processing apparatus, comprising:

a memory for storing one or more angiographic parameter imaging (API) maps of a vasculature, wherein each API map of the one or more API maps encodes a hemodynamic parameter comprising one or more of time to peak (TTP), mean transit time (MTT), time to arrival, peak height (PH), and/or area under the time-density curve (AUC); and a processor in electronic communication with the memory, and wherein the processor is programmed to determine a state of the vasculature based on the one or more API maps stored in the memory, and wherein the processor determines the state of the vasculature using a machine-learning classifier trained to determine a reperfusion state of the vasculature, an occlusion state of the vasculature, or both; and wherein the processor is programmed to display a vasculature state assessment based on the determined state of the vasculature to provide feedback for adjusting the endovascular procedure, wherein the vasculature state assessment includes a probability of achieving a relevant therapeutic outcome as defined by established clinical standards.

19. The image processing apparatus of claim 18, wherein the processor is further programmed to obtain the one or more API maps and store the one or more API maps in the memory.

20. The image processing apparatus of claim 18, wherein the processor is further programmed to:

obtain one or more digital subtraction angiography (DSA) image sequences;

generate one or more API maps from the one or more DSA image sequences, wherein each API map corresponds to a DSA image sequence; and store the generated one or more API maps in the memory.

21. The image processing apparatus of claim 20, wherein the processor generates each API map by temporally cropping the DSA image sequence to only include frames where contrast is shown in a capillary phase.

22. The image processing apparatus of claim 20, wherein the processor generates each API map by spatially cropping each image of the DSA image sequence to remove portions outside a region of interest.

23. The image processing apparatus of claim 20, wherein the processor generates each API map by extracting a time density curve at each pixel of the DSA image sequence.

24. The image processing apparatus of claim 20, further comprising an imaging sensor in electronic communication with the processor, and wherein the processor is further programmed to generate the one or more DSA image sequences using the imaging sensor.

25. The image processing apparatus of claim 18, wherein the machine-learning classifier of the processor is trained to determine an occlusion state of a vasculature.

26. The image processing apparatus of claim 18, wherein the machine-learning classifier of the processor is trained to determine a reperfusion state of the vasculature.

27. The image processing apparatus of claim 18, wherein the machine-learning classifier of the processor is a convolutional neural network (CNN).

28. The image processing apparatus of claim 27, wherein the CNN comprises ensemble networks.

29. The image processing apparatus of claim 28, wherein a first network of the ensemble networks is trained using anterior-posterior API maps and a second network of the ensemble networks is trained using lateral API maps, and the processor is programmed to determine the state of the vasculature using a combination of results from each network of the ensemble networks.

30. The image processing apparatus of claim 29, wherein the processor is further programmed to weight a result of each network by a network coefficient.

31. The image processing apparatus of claim 18, wherein the processor is further programmed to normalize the hemodynamic parameter to reduce injection variability.

32. The image processing apparatus of claim 18, wherein the processor is further programmed to correct the one or more API maps to account for C-arm position to reduce foreshortening error.

33. The image processing apparatus of claim 18, wherein the one or more API maps comprise a pre-treatment API map and a post-treatment API map.

34. The image processing apparatus of claim 18, wherein the processor is further programmed to segment the one or more API maps using a CNN.

\*  \*  \*  \*  \*